US008895812B2

(12) United States Patent
Hofstede et al.

(10) Patent No.: US 8,895,812 B2
(45) Date of Patent: Nov. 25, 2014

(54) DISEASE RESISTANT CUCUMBER PLANTS

(75) Inventors: René Johannes Maria Hofstede, Boven-Leeuwen (NL); Wouter Pieter Johannes De Ruiter, Bergschenhoek (NL)

(73) Assignee: Monsanto Invest B.V., Bergschenhoek (NL)

( * ) Notice: Subject to any disclaimer, the term of this patent is extended or adjusted under 35 U.S.C. 154(b) by 753 days.

(21) Appl. No.: 12/112,519

(22) Filed: Apr. 30, 2008

(65) Prior Publication Data
US 2008/0307540 A1 Dec. 11, 2008

Related U.S. Application Data

(63) Continuation of application No. PCT/NL2006/000553, filed on Nov. 6, 2006.

(30) Foreign Application Priority Data

Nov. 4, 2005 (EP) ..................... 05077528

(51) Int. Cl.
A01H 1/02 (2006.01)
A01H 1/04 (2006.01)
A01H 5/08 (2006.01)
C12N 15/82 (2006.01)
C12Q 1/68 (2006.01)

(52) U.S. Cl.
CPC ............. *C12Q 1/6895* (2013.01); *A01H 5/08* (2013.01); *C12N 15/8282* (2013.01); *C12N 15/8283* (2013.01); *A01H 1/04* (2013.01)
USPC ........... 800/307; 800/266; 800/265; 800/267; 435/6.11

(58) Field of Classification Search
None
See application file for complete search history.

(56) References Cited

U.S. PATENT DOCUMENTS 4,458,066 A 7/1984 Caruthers et al.
5,591,616 A 1/1997 Hiei et al.

FOREIGN PATENT DOCUMENTS

EP 1 188 833 A1 3/2002
WO WO 02/22836 A2 3/2002

OTHER PUBLICATIONS

Karasev et al. Annu. Rev. Phytopathol., (2000) 38, pp. 293-324.*
Bai et al., "QTLs for tomato powdery mildew resistance (*Oidium lycopersici*) in Lycopersicon parviflorum G1.1601 co-localize with two qualitative powdery mildew resistance genes," *Mol. Plant Microbe Interactions*, 16:169-176 (2003).
Fanourakis "Inheritance and linkage studies of the fruit epidermis structure and investigation of linkage relations of several traits and of meiosis in cucumber," Ph.D. Diss., Univ. of Wisconsin, Madison (1984).
Fazio et al., "Genetic mapping and QTL analysis of horticultural traits in cucumber *Cucumis sativus* L.), using recombinant inbred lines," *Theor. Appl. Gen.*, 107(5):864-874 (2003).
Horejsi et al, "Linkage of random amplified polymorphic DNA markers to downy mildew resistance in cucumber (*Cucumis sativus* L.)," *Euphytica*,115 (2):105-113 (2000).
Hujieda and Akya, "Inheritance of powdery mildew resistance and spine color of fruit in cucumber," *J. Jpn. Soc. Hort. Sci.*, 31:30-32 (1962).
Kooistra, "Powdery mildew resistance in cucumber," *Euphytica*, 17:236-244 (1968).
Kooistra, "Inheritance of flesh and skin colors in powdery mildew resistant cucumbers (*Cucumis sativus* L.)," *Euphytica*, 20:521-523 (1971).
Morishita et al., "Review: Powdery Mildew Resistance in Cucumber," JARQ, 37(1):7-14 (2003).
Nesbitt and Tanksley, "fw2.2 directly affects the size of developing tomato fruit, with secondary effects on fruit number and photosynthate distribution," *Plant Physiol.*, 127:575-583 (2001).
Sakata et al., "QTL analysis of powdery mildew resistance in cucumber (*Cucumis sativus* L.)," *Theor. Application. Gen.*, 112(2):243-250 (2005).
Shanmugasundarum et al., "Inheritance of resistance to powdery mildew in cucumber," *Phytopathology* 61:1218-1221 (1971).
Shanmugasundarum et al., "A recessive cotyledon marker gene in cucumber with pleiotropic effects.," *HortScience* 7:555-556 (1972).

(Continued)

*Primary Examiner* — Brent T Page
*Assistant Examiner* — Jared Shapiro
(74) *Attorney, Agent, or Firm* — Dentons US LLP

(57) ABSTRACT

The present invention relates to a plant that is resistant to cucumber closterovirus and resistant to cucumber powdery mildew, wherein said plant is a plant of the species *Cucumis sativus*, said plant comprising, on a single chromosome, at least one chromosomal region that confers closterovirus resistance and at least one chromosomal region that confers powdery mildew resistance,
wherein said at least one region that confers closterovirus resistance is linked to at least one marker selected from the group consisting of markers E16/M50-244, E16/M50-188, and E11/M48-251, and
wherein said at least one region that confers powdery mildew resistance is linked to at least one marker selected from the group consisting of:
the single nucleotide polymorphism marker 39T→G in SEQ ID NO:1,
the single nucleotide polymorphism marker 29G→A in SEQ ID NO:2,
the single nucleotide polymorphism marker 193C→T in SEQ ID NO:3,
the insertion mutation 5'-AATTT-3' at position 221 in SEQ ID NO:4, and
markers E16/M50-F-194, E11/M48-F-251, E23/M38-M001, E23/M40-M003, E24/M46-M002, E24/M46-M003, E12/M91-M003, E26/M43-M003, E14/M59-F-134 and E14/M59-F-200.

22 Claims, 8 Drawing Sheets

(56) References Cited

OTHER PUBLICATIONS

Walters et al., "Segregation and linkage of several genes in cucumber," *J. Am. Soc. Hort. Sci.*, 126(4):442-450 (2001).
Xie and Wehner, "Gene list 2001 for Cucumber," retrieved from the Internet: URL: http://www.umreasearch.umd.edu/CGC/genelist/cucumber.pdf.
Zijlstra et al., "Search for Novel Genes for resistance to Powdery Mildew . . . ," *Euphytica*, Kluwer Academic Press, Amsterdam, NL, 64(1-2):31-37 (1992).
Accession No. PI 197088.
Accession No. PI 200815.
Accession No. PI 200818.
Accession No. PI 250147.
Accession No. PI 279465.
Zijlstra et al., "The relationship between powdery mildew (*Sphaerotheca fuliginea*) resistance and leaf chlorosis sensitivity in cucumber (*Cucumis sativus*) studied in single seed descent lines," *Euphytica* 81:193-198, 1995.

\* cited by examiner

SEQ ID NO. 1
```
  1 GTCGTCTTCGCCTATGCAGACAAAATAAATGCTTGTTTGAGTCTAGCCAA  50
 51 AAATGGTGTAGAACAGTTGATCACAGTTCCTACGGACTATAACATTAGAA 100
101 ACACCTTTGACAAATTTTCTGTGTTTTGCATAGACCATAGTGGTAATTGA 150
151 CAGGCG
```

SEQ ID NO. 2
```
  1 TCATAATGACACGTAATGATTGTCAGAGAAAATTTATAGAAACCTTTTGT  50
 51 TCAACTATCCAACAAATTACAATCAAGGCACTTCTGGAATGAGATAGTCA 100
101 GCTGCTAAGCAGATCTCAAAGGGAGAAGAGAAAAATATTCACATCACAGA 150
151 CTATAACAAAGGTTTGAATCTTAAGGCCAACAAACAACTTTGTAGATGTC 200
201 AAAAAAAATGTACGAAATAAACGATAAAGATGCATGTCTCTCTTTCTA 250
251 GATGAATTATCAAAGATCTCTGACTACAAGAGGGGATATA
```

SEQ ID NO. 3
```
  1 TTTTTATCTTCTCCCAAGTACCGCAACCGAGAGGATTCATCTTCATGTTC  50
 51 TTCCAAGTGCCACAGCCAGAGGATTTATCTTCACCTTCCCCCATGTGTTG 100
101 CARCCGAGAGGATTCATCTTCAGCTTCTCTCAGGTGCCGCAATCGAGAGG 150
151 ATTCATGTTCATCTTCTCCCAGGTGCTACAATCGAAAGAATTTATCTTCA 200
201 TCTTCTCTTAGGKGCCACAATCGAGAGGGTTTATCTTCATCTTTCCTCAT 250
251 GTGTGGCAACCGA
```

SEQ ID NO. 4
```
  1 TCGATAATTCAGGCTCGCAACTCAAATTGCATTGAGAATCTTTTAGGGAG  50
 51 AAGTATGTATTATAGCAGAGGATGAGGATCAGAGAATATTGAGATCGTCG 100
101 TAGTTAGGATCAAAGTGAACCCACGGATTGATTGACTGGATCCGGTAGGA 150
151 TGAAGGCCTTTGACTTAGTGGATAAGAGAGGTCCTTGTAAAATATTATTT 200
201 TTCATTTAGACCTTGATTTTAATTTGGACTATGAATCATATTTGACAATT 300
301 GTAGGATCAAACCGAAGGTGCAAAGAATATT
```

Fig. 8

DISEASE RESISTANT CUCUMBER PLANTS

RELATED APPLICATIONS

This application is a continuation of PCT application no. PCT/NL2006/000553, designating the United States and filed Nov. 6, 2006; which claims the benefit of the filing date of European application no. EP 05077528.7, filed Nov. 4, 2005; each of which is hereby incorporated herein by reference in its entirety for all purposes.

FIELD OF THE INVENTION

The present invention is in the field of disease resistant plants and plant breeding, more in particular to breeding of powdery mildew and closterovirus-resistant cucumber plants.

BACKGROUND OF THE INVENTION

Commercial cucumber (*Cucumis sativus*) production can suffer from a variety of diseases. Yellowing viruses cause one such disease and may cause significant economic damage in cucumber production. The family of closteroviruses (Closteroviridae), which forms the highest taxonomic cluster of Yellowing viruses affecting cucumber, comprises more than 30 flexuous and filamentous, insect-transmitted plant viruses. The family consists of three genera, of which the whitefly-transmitted *Crinivirus* genus comprises species that are of particular concern to cucumber. This genus includes inter alia the species *Cucurbit yellow stunting disorder virus* (CYSDV), *Lettuce infectious yellows virus* (LIYV) and *Beet pseudo-yellows virus* (BPYV). CYSDV and BPYV pose the biggest threats to cucumber growers.

The viruses normally reside in the insect vector and are transmitted by the feeding activity of the insects on the plant. Cucumber closterovirus may therefore be controlled by means of application of insecticides. Preferably however, control of closterovirus in agriculture and horticulture is achieved by providing virus resistant cultivars of the host plants. At present, at least two quantitative trait loci or QTLs in the genome of resistant cucumber varieties are recognized as being associated with closterovirus resistance in cucumber (vide WO 02/22836). Proper introgression of the genetic material associated with closterovirus resistance into offspring plant lines may thus be monitored by detecting specific markers linked with these QTLs. Knowledge of the QTLs may therefore assist in the breeding of closterovirus resistant cultivars.

Another important disease that affects commercial cucumber production is cucumber powdery mildew (PM). PM in cucurbits may be caused by the fungi *S. fuliginea* and *E. cichoracearum*. The disease is widespread and can occur year-round. Symptoms start as small spots of a fine white fungal thread on the surface of infected leaves, which spots may grow out and eventually cover stems and foliage with a white, powdery mass of spores and hyphae. Severe infection results in discoloring and loss of leaves, with a concomitant reduction in the number and size of the fruits. Although a number of fungicides are effective against powdery mildew, resistance of the fungus towards the chemicals is emerging.

Various cucumber strains exhibit some level of resistance to powdery mildew. Such strains include for instance the Indian wild cucumber accession PI 197088, and accessions PI 200815, PI 200818, as well as the cultivars Natsufushinari and Asomidori (Morishita et al. 2003). Also various genes associated with resistance to PM are known (Fanourakis, 1984; Hujieda and Akiya, 1962; Kooistra, 1968, 1971; Shanmugasundarum et al., 1971, 1972), including pm-1 and pm-2 in Natsufushinari, pm-3 in PI 200815 and PI 200818 and "pm-h" in the cultigen Wis. SMR 18 (gene "pm-h" is without prejudice to the pm locus indicated by pm-h herein below). Although a few commercial cucumber varieties are available with partial tolerance to PM, most commercial growers still rely on the use of foliar fungicides. This is in part due to the fact that PM resistance is difficult to introduce into lines that exhibit other types of resistance. For instance, it has occurred to breeders as a disadvantage that lines acquiring PM resistance alleles become susceptible to closterovirus and vice versa, whereas previously they were not. In fact, crossing experiments have thus far not resulted in cucumber lines that exhibit resistance to both PM and closteroviruses. The beneficial double resistant recombinants have thus far not been attained. This is surprising, since by and large the merging of different traits into a single genome may be accomplished by relatively straightforward breeding procedures.

It is an object of the present invention to provide cucumber plants which exhibit resistant to viruses of the family of closteroviruses that affect cucumber, in particular BPYV and CYSDV, and which plant in addition thereto exhibits resistance to cucumber powdery mildew brought about by the fungi *S. fuliginea* and/or *E. cichoracearum*.

SUMMARY OF THE INVENTION

The present inventors have now found a number of cucumber plants that exhibit resistance to both CYSDV and PM. Moreover, they discovered that these double-resistant cucumber plants comprised two quantitative trait loci (QTLs) associated with powdery mildew resistance (pm-l and pm-h as described herein) as well as one major QTL associated with closterovirus resistance (QTL-1 as described herein). More importantly, they discovered that all QTLs were located in a single genetic linkage group. Thus, the present inventors essentially discovered that in these plants, the genes for resistance to closterovirus and powdery mildew resided on a single chromosome. Such plants are very advantageous for use in plant breeding. Moreover, the inventors discovered a possible mechanism why the double resistant cucumber plants could not previously be obtained by crossing experiments. Without wishing to be bound by theory it is believed that introgression of a genetic element essential for resistance to one disease resulted in loss of the genetic element essential for resistance to the other disease. By this discovery, the inventors have developed breeding schemes by which this problem could be solved thereby obtaining the required double-resistant plants.

In a first aspect, the present invention provides a plant of the species *Cucumis sativus* which plant exhibits resistance to cucumber closteroviruses as well as resistance to cucumber powdery mildew.

In a preferred embodiment of such a plant of the invention, the genomic region(s) responsible for the closterovirus-resistance (QTL-1) and the genomic region(s) responsible for the powdery mildew resistance (pm-h and/or pm-l) are present on a single chromosome. In an even more preferred embodiment of such a plant, pm-h and pm-l are both present and QTL-1 is positioned in between pm-h and pm-l.

In a further embodiment of a plant of the invention, the presence of QTL-1 is indicated by the presence of at least one flanking marker selected from the group consisting of markers E16/M50-244, E16/M50-188, and E11/M48-251 as described in more detail in WO 02/22836, to which express reference is made in this context.

In another embodiment of a plant of the invention, the presence of the QTL referred to as pm-h is indicated by the presence of a nucleic acid sequence comprising at least one mutation resulting from a single nucleotide polymorphism (SNP) associated with the powdery mildew resistance in said plant, wherein said at least one single nucleotide polymorphism (SNP) is selected from SNP 1 and SNP 2 as shown in Table 2 below.

In another embodiment of a plant of the invention, the presence of QTL referred to as pm-l is indicated by the presence of a nucleic acid sequence comprising at least one mutation resulting from a single nucleotide polymorphism (SNP) indicated as SNP 3 in Table 3 below associated with the powdery mildew resistance in said plant, or comprising at least one mutation indicated as the 5-bp insertion 5'-AATTT-3' in Table 3 below associated with the powdery mildew resistance in said plant.

The invention thus preferably provides a plant that is resistant to cucumber closterovirus and to cucumber powdery mildew, wherein said plant is a plant of the species *Cucumis sativus*, said plant comprising, on a single chromosome, at least one chromosomal region that confers closterovirus resistance and at least one chromosomal region that confers powdery mildew resistance, wherein said at least one region that confers closterovirus resistance is linked to at least one marker selected from the group consisting of markers E16/M50-244, E16/M50-188, and E11/M48-251, and wherein said at least one region that confers powdery mildew resistance is linked to at least one marker selected from the group consisting of:

the single nucleotide polymorphism marker 39T→G in SEQ ID NO:1,
the single nucleotide polymorphism marker 29G→A in SEQ ID NO:2,
the single nucleotide polymorphism marker 193C→T in SEQ ID NO:3,
the insertion mutation 5'-AATTT-3' at position 221 in SEQ ID NO:4, and
markers E16/M50-F-194, E11/M48-F-251, E23/M38-M001, E23/M40-M003, E24/M46-M002, E24/M46-M003, E12/M91-M003, E26/M43-M003, E14/M59-F-134 and E14/M59-F-200.

A plant of the invention may optionally comprise a second QTL associated with closterovirus resistance (QTL-2 as described in WO 02/22836, reference is made explicitly to the specification of this document for the details on the localization and characteristics of this QTL). This QTL was shown to be located on a separate chromosome.

In another aspect, the invention provides a part of a cucumber plant of the invention as defined above. Preferably, said plant part is selected from pollen, ovules, leaves, embryos, roots, root tips, anthers, flowers, fruits, stems, shoots, scions, rootstocks, seeds, protoplasts and calli, and is most preferably seed.

In another aspect, the invention provides F1 seed obtained by crossing a double (closterovirus plus PM resistance [including both PM-leaf (pm-l) and PM-hypocotyl (pm-h) resistant phenotype]) resistant cucumber plant of the invention as described above with a second cucumber plant or other plant variety, preferably a plant of a cucumber line that comprises commercially desirable characteristics. Preferably, said second cucumber plant at least comprises pm-h as this is a recessive gene. Said second cucumber plant is in that case at least heterozygous, preferably homozygous for the recessive pm-h trait. In another preferred embodiment, said second cucumber plant is susceptible to closterovirus and is more preferably an inbred plant.

In another aspect, the invention provides a hybrid plant obtained by growing the F1 seed of the invention as defined above.

In another aspect, the invention provides a part of the hybrid plant of the invention as defined above. Preferably said plant part is selected from pollen, ovules, leaves, embryos, roots, root tips, anthers, flowers, fruits, stems, shoots, scions, rootstocks, seeds, protoplasts and calli, and is most preferably fruits.

As stated above, introgression of a genetic element essential for resistance PM or closterovirus by crossing of plants that are each resistant to only one of the diseases, is believed to result in loss of the genetic element essential for resistance to the other disease. By this discovery, the inventors have developed breeding schemes by which this problem could be solved, thereby obtaining the required double-resistant plants. The present inventors discovered that in order to effectively produce double-resistant cucumber plants from a cross between a plant of closterovirus-resistant parent cucumber line wherein said resistance is brought about by QTL-1, and a plant of a PM-resistant cucumber line wherein said resistance is brought about by pm-h and pm-l, the breeding process must comprise the step of permitting the formation of recombinants (i.e. allow for the occurrence of homologous recombination events in one chromosome), followed by the step of selecting plants having QTL-1 and pm-l or QTL-1 and pm-h in a single chromosome. Preferably, said selection step comprises the selection of plants having QTL-1, pm-l and pm-h in a single chromosome. More preferably still, QTL-1 is introgressed in a genomic region in between the genomic regions harboring pm-h and pm-l, so that, effectively, QTL 1 for closterovirus resistance is sandwiched in between two QTLs for PM resistance.

Identifying the presence of any of the QTL's as defined herein associated with resistance to PM or closterovirus may occur by detecting one or more genetic markers linked to the respective QTL on the chromosome of the plant, genetic markers in linkage disequilibrium with the respective QTL on the chromosome of the plant, or combinations thereof.

A suitable method for detection of the presence and/or position of said QTLs in said plants comprises the use of AFLP markers characterizing said QTLs. Preferably said step of selecting plants having QTL-1, pm-l and/or pm-h in a single chromosome comprises the detection of at least one AFLP marker characterizing the quantitative trait locus QTL-1 associated with closterovirus-resistance on the same chromosome that harbors the quantitative trait locus (QTL) for pm-l or, alternatively, on the same chromosome that harbors the quantitative trait locus (QTL) for pm-h associated with PM-resistance, preferably on the same chromosome that harbors both quantitative trait loci pm-h and pm-l, in which case said QTL-1 marker is located in a chromosomal region between QTL pm-h and QTL pm-l. Thus, the selection process may involve the detection of one or more markers selected from the group of markers consisting of the markers of table 2, 3 and 4.

In another aspect, the present invention provides a method for selecting a plant of the species *Cucumis sativus* exhibiting resistance towards cucumber closterovirus and cucumber powdery mildew comprising detecting in said plant the presence on a single chromosome of QTL-1, and at least one of the QTLs pm-l and pm-h.

In one embodiment of such a method the method comprises the steps of:

a) providing a sample of genomic DNA from a cucumber plant, said sample comprising genomic DNA fragments of sufficient length;

b) performing a purification reaction to select fragments that comprise at least a first QTL, or a molecular marker associated therewith, from the group consisting of QTL-1, pm-l and pm-h;

c) performing a nucleic acid amplification reaction on said selected fragments to detect fragments that comprise at least a second QTL, or a molecular marker associated therewith, from the group consisting of QTL-1, pm-l and pm-h, and d) detecting in the reaction product of step c) an amplified DNA fragment having the predicted length or the predicted nucleic acid sequence.

In a preferred embodiment, said step b) comprises the use of at least one set of primers defining a molecular marker for said first QTL, or at least one nucleic acid probe having a base sequence which is substantially complementary to the nucleic acid sequence defining said marker and which nucleic acid probe specifically hybridizes under stringent hybridization conditions with a nucleic acid sequence defining said marker(s).

In another preferred embodiment, said step c) comprises the use of at least one set of primers defining a molecular marker for said second QTL, or at least one set of primers which specifically hybridize under stringent conditions with a nucleic acid sequence of a molecular marker for said second QTL.

In another embodiment of a method of the invention, the step of detecting in said plant the presence of said QTLs on a single chromosome is performed by using in situ hybridization techniques or in situ amplification techniques. Again, probes and primers defining a molecular marker for said QTLs or which specifically hybridize under stringent conditions with a nucleic acid sequence of a molecular marker for said QTL are suitably used in such methods.

In aspects of the invention, molecular markers are preferably SNPs, insertion mutation markers or AFLP markers, more preferably markers selected from the group consisting of the markers listed in Tables 2-4 as well as those from literature references expressly cited for that purpose herein.

In another aspect, the present invention provides a method of producing a plant of the species *Cucumis sativus* which plant exhibits resistance to cucumber closterovirus and to cucumber powdery mildew, comprising the steps of:

a) selecting a first cucumber plant that comprises a chromosomal region that confers resistance to cucumber closterovirus, by detecting in the genome of said plant the presence of at least one marker linked to the cucumber closterovirus resistance-conferring QTL indicated by markers E16/M50-244, E16/M50-188, and E11/M48-251;

b) selecting a second cucumber plant that comprises at least one chromosomal region that confers resistance to cucumber powdery mildew by detecting in the genome of said plant the presence of at least one marker linked to a first cucumber powdery mildew resistance-conferring QTL indicated by the following markers:

the single nucleotide polymorphism marker 39T→G in SEQ ID NO:1,
the single nucleotide polymorphism marker 29G→A in SEQ ID NO:2, and
markers E16/M50-F-194, E11/M48-F-251, and E23/M38-M001; or
by detecting in the genome of said plant the presence of at least one marker linked to a second cucumber powdery mildew resistance-conferring QTL indicated by the following markers:
the single nucleotide polymorphism marker 193C→T in SEQ ID NO:3,
the insertion mutation 5'-AATTT-3' at position 221 in SEQ ID NO:4, and
markers E23/M40-M003, E24/M46-M002, E24/M46-M003, E12/M91-M003, E26/M43-M003, E14/M59-F-134 and E14/M59-F-200;

c) crossing said plants from step a) and step b) to produce F1 seeds;

d) growing an amount of F1 seeds into F1 plants, generating a further offspring population from said F1 plants by crossing or selfing, and e) selecting from among said further offspring plants a plant that comprises at least one marker linked to the cucumber closterovirus resistance-conferring QTL as defined in step a) and at least one marker linked to the cucumber powdery mildew resistance-conferring QTL as defined in step b).

The skilled artisan will understand that said further offspring population should be of sufficient size to allow the detection of the presence of plants in among said further offspring population that have undergone at least two homologous recombination events in a single chromosome. Generally, a population of about a 1,000 plants will be sufficient. An advantage of the presently proposed marker selection technique, is that such population sizes can easily be screened for the presence of geneotypes of interest, which may phenotypically be undetectable.

In a preferred embodiment of this method the step of selecting a second cucumber plant in step b) comprises selecting a second cucumber plant having only one of said first or second cucumber powdery mildew resistance-conferring QTLs, and wherein said method further comprises the step of:

f) selecting a third cucumber plant having another of said first or second cucumber powdery mildew resistance-conferring QTLs (i.e. a QTL which is not present in said second cucumber plant);

g) crossing the F1 plants obtained in step e) with said third cucumber plant to produce further offspring plants, and h) selecting from among the offspring plants a plant that comprises the cucumber closterovirus resistance-conferring QTL as defined in step a) and both the cucumber powdery mildew resistance-conferring QTLs as defined in step b).

In a preferred embodiment, plants are selected which comprise both powdery mildew resistance conferring loci pm-h and pm-l and wherein the closterovirus resistance conferring locus characterized by QTL-1 is positioned in between both powdery mildew resistance conferring loci pm-h and pm-l.

Thus, in another preferred embodiment of a method of producing a plant of the species *Cucumis sativus* that exhibits resistance to cucumber closterovirus and to cucumber powdery mildew, the step of selecting a cucumber plant that comprises a chromosomal region that confers resistance to cucumber powdery mildew as defined in steps b), e), f) or h) comprises:

detecting the presence in the genome of said plant of at least one marker linked a first cucumber powdery mildew resistance-conferring QTL indicated by SNP marker 39T→G in SEQ ID NO:1, SNP marker 29G→A in SEQ ID NO:2, and markers E16/M50-F-194, E11/M48-F-251, and E23/M38-M001; and detecting in the genome of said plant the presence of at least one marker linked to a second cucumber powdery mildew resistance-conferring QTL indicated by SNP marker 193C→T in SEQ ID NO:3, insertion mutation 5'-AATTT-3' at position 221 in SEQ ID NO:4, and markers E23/M40-M003, E24/M46-M002, E24/M46-M003, E12/M91-M003, E26/M43-M003, E14/M59-F-134 and E14/M59-F-200.

In another preferred embodiment of a method of producing a plant of the species *Cucumis sativus* that exhibits resistance to cucumber closterovirus and to cucumber powdery mildew, at least one of steps a), b), e), f) or h) comprise the step of providing a sample of genomic DNA from said plant and detecting in said sample of genomic DNA said at least one marker.

In an alternative preferred embodiment step e) comprises detecting in the genome of plants at least one marker associated with QTL-1 and at least one marker associated with pm-h or pm-l, preferably detecting in the genome of plants and on a single chromosome at least one marker associated with QTL-1, at least one marker associated with pm-h and at least one marker associated with pm-l, preferably comprising the markers as selected from the group of markers listed in Tables 2, 3 and 4.

In another preferred embodiment step e) is performed by the method of the invention for selecting a double-resistant plant of the species *Cucumis sativus* as described above.

It will be understood that the process as described in steps c)-e) wherein at least two homologous recombination events in a single chromosome have occurred in a single crossing that produces the double-resistant F1, may also be achieved over multiple generations, such that the proposed (at least two) homologous recombination events in a single chromosome, and thus the formation of the double resistant plant, is realized in the F2, F3, F4, F5 or any subsequent generation. Such variations are within the scope of the presently claimed invention, and can easily be attained by the skilled person.

In an alternative method of producing a plant of the species *Cucumis sativus* which exhibits resistance to cucumber closterovirus and to cucumber powdery mildew, the method may comprise the steps of:

a) selecting a first plant of the species *Cucumis sativus* exhibiting resistance towards cucumber closterovirus and cucumber powdery mildew by performing the method of the invention;

b) inbreeding said plant to produce a plant line homozygous for said QTLs c) crossing said plants from step a) and step b) to produce F1 seeds;

d) growing said F1 seeds into F1 plants.

Another aspect of the invention is the plants produced by the methods of the invention, or parts thereof.

The present invention now allows for very rapid screening of offspring plants in order to select plants likely to exhibit double resistance. For instance, one may detect amongst offspring plants those plants that have at least one of the pm-h markers, at least one of the pm-l markers and at least one of the QTL-1 markers. Such plants are likely to have acquired the desirable introgression. Screening for additional markers may raise the level of confidence on the prediction that an offspring plant exhibits double resistance. Upon detection of plants exhibiting at least one marker for each of the three QTLs the plant may be selected and used in breeding programs, or in additional characterization experiments.

An advantage of the plants of the present invention wherein the traits are located on one and the same chromosome is that they provide for improved possibilities to move the genes that control both forms of resistance more easily into other (hybrid) plants when using conventional breeding, whereas if the traits were to be located on separate chromosomes, it would be much more difficult to produce hybrids comprising both traits in combination by using conventional breeding techniques.

DESCRIPTION OF THE DRAWINGS

FIG. 8 shows the DNA sequence in the vicinity of SNP and insertion markers as indicated by the respective SEQ IDs in Tables 2 and 3 herein.

DETAILED DESCRIPTION OF THE INVENTION

Definitions

Figure 1:
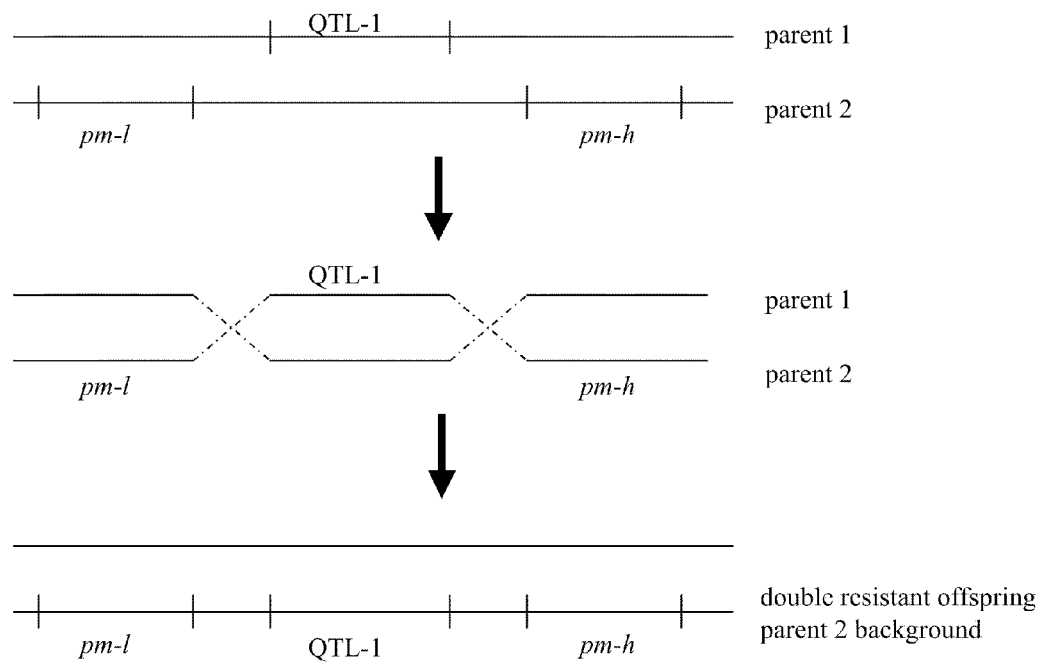
FIGS. 1-6 shows a number of possible recombination scenario wherein powdery mildew (pm) and closterovirus (QTL-1) resistance from two separate plants is combined into a single offspring plant. It should be understood that the various parents indicated as having multiple resistance loci may themselves be the result of crossings or selfings. Thus, a plant having both QTLs pm-l and pm-h may be obtained by crossing of plants having a single QTL.

The term "cucumber" as used herein refers to a plant, or a part thereof, of the species *Cucumis sativus* including, but not limited to, plants commonly referred to as Cucumber, American gherkin, Cassabanana, Cuke, Gherkin, Hothouse cucumber, Lemon cucumber, Mandera cucumber, Pickling cucumber, Serpent cucumber, Slicing cucumber, Snake cucumber, and West Indian gherkin.

As used herein, the term "plant part" indicates a part of a plant, including single cells and cell tissues such as plant cells that are intact in plants, cell clumps and tissue cultures from which plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

The term "closterovirus" as used herein refers to a virus of the family of Closteriviridae including, but not limited to, viruses commonly referred to as Cucurbit yellow stunting disorder virus (CYSDV), Lettuce infectious yellows virus (LIYV) and Beet pseudo-yellows virus (BPYV; also known under its synonyms Cucumber chlorotic spot virus (CCSV), Cucumber yellows virus, Muskmelon yellows virus or Strawberry pallidosis virus), preferably BPYV and CYSDV, most preferably CYSDV. Preferably, in relation to cucumber plants, the term "closterovirus" refers to the genus of special importance to cucumber plants, i.e. the Criniviideae.

The term "powdery mildew" as used herein refers to the fungal disease caused in cucumber (*Cucumis sativis* L.) by the fungus *Sphaerotheca fuliginea* (also known by its synonyms *Podosphaera xanthii* and *S. cucurbitae*) and/or by the fungus *Erysiphe cichoracearum* (also known by its synonym *Golovinomyces cichoracearum*) and/or by the fungus *Leveillula taurica* (also known by its synonyms *Oidiopsis taurica, Erysiphe taurica, Ovulariopsis cynarea, Leveillula solanacearum*).

The term "QTL" is used herein in its art-recognized meaning of a chromosomal region containing alleles (e.g. in the form of genes or regulatory sequences) associated with the expression of a continuously distributed (quantitative) phenotypic trait. The term "QTL for disease resistance" refers to a region located on a particular chromosome that is associated with at least one gene that encodes for resistance or at least a regulatory region, i.e. a region of a chromosome that controls the expression of one or more genes involved in resistance. To address QTLs associated with resistance, the shorter equivalent: "resistance conferring locus" is used herein. The QTLs may be defined by indicating their genetic location in the genome of a specific *Cucumis sativus* accession using one or more molecular genomic markers. One or more markers, in turn, indicate a specific locus. Distances between loci are usually measured by the frequency of crossing-overs between loci on the same chromosome. The farther apart two loci are, the more likely that a crossing-over will occur between them. Conversely, if two loci are close together, a crossing-over is less likely to occur (between them). As a rule, one centimorgan (Kosambi map function (cM)) is approximately equal to 1% recombination between loci (markers) (Lui, 1997). When a QTL can be indicated by multiple markers the genetic distance between the end-point markers is indicative of the size of the QTL.

The term "chromosome" is used herein in its art-recognized meaning of the self-replicating genetic structure in the cellular nucleus containing the cellular DNA and bearing in its nucleotide sequence the linear array of genes.

As used herein, the term "linkage group" refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous to (the physical entity of) chromosome.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present invention relates to QTLs, i.e. genomic regions that may comprise one or more genes or regulatory sequences, it is in some instances more accurate to refer to "haplotype" (i.e. an allele of a chromosomal segment) in stead of "allele," however, in those instances, the term "allele" should be understood to comprise the term "haplotype."

A "gene" is defined herein as a hereditary unit consisting of a sequence of DNA that occupies a specific location on a chromosome and that contains the genetic instruction for a particular characteristics or trait in an organism.

A "locus" is defined herein as the position that a given gene or a regulatory sequence occupies on a chromosome of a given species.

"Homologous recombination" is the exchange ("crossing over") of DNA fragments between two DNA molecules or chromatids of paired chromosomes over in a region of identical nucleotide sequences. A "recombination event" is herein understood to mean a meiotic crossing-over.

As used herein, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. A "molecular marker linked to a QTL" as defined herein may thus refer to SNPs, insertion mutations as well as more usual AFLP markers or any other type of marker used in the field. In the context of AFLP markers named herein the markers indicate a cucumber-specific DNA sequence flanked by two AFLP-primers, which primers consist of "core primers" E and M, corresponding with the restriction sites of the restriction enzymes EcoRI and MseI, (Vos et al., 1995; Bai et al. 2003) followed by 2 or 3 extra selective bases as indicated, each followed by a two-digit code identifying the selective nucleotides by which the "core primer" is extended (for code see Table 1). E16/M50-244 represents a marker obtained by using amplification primers EcoRI+CC and MseI+CAT to produce a fragment having a total length of 244 bp. The length of the fragment may depend on the method used to detect the fragment, and is an approximation of its true length, plus or minus a few bases. In defining a marker as provided herein reference should be made to the position on the chromosome of that marker relative to other markers in a linkage map. Thus, marker E16/M50-244 is defined both by the sequence of its primers, as well as by its length as an amplification product, and by its position relative to E14/M59-F-200 and/or E23/M38-M003 or, as provided herein, by its position relative to other markers as depicted in the ordered listing with corresponding distance in cM in the matrix of Table 4. It should however be taken into consideration that crossings between plants can result in certain markers being lost, so that the absence of a certain marker does not rule out the presence of the genetic element that confers resistance to disease and to which that marker is said to be linked.

TABLE 1

Primer extension codes as generally applied in AFLP analyses, and as used herein (Source: Keygene, Wageningen, The Netherlands)

| Primer-code | Extension |
|---|---|
| 01 | A |
| 02 | C |
| 03 | G |
| 04 | T |
| 11 | AA |
| 12 | AC |
| 13 | AG |
| 14 | AT |
| 15 | CA |
| 16 | CC |
| 17 | CG |
| 18 | CT |
| 19 | GA |
| 20 | GC |
| 21 | GG |
| 22 | GT |
| 23 | TA |
| 24 | TC |
| 25 | TG |
| 26 | TT |
| 31 | AAA |
| 32 | AAC |
| 33 | AAG |
| 34 | AAT |
| 35 | ACA |
| 36 | ACC |
| 37 | ACG |

TABLE 1-continued

Primer extension codes as generally applied in AFLP analyses, and as used herein (Source: Keygene, Wageningen, The Netherlands)

| Primer-code | Extension |
| --- | --- |
| 38 | ACT |
| 39 | AGA |
| 40 | AGC |
| 41 | AGG |
| 42 | ACT |
| 43 | ATA |
| 44 | ATC |
| 45 | ATG |
| 46 | ATT |
| 47 | CAA |
| 48 | CAC |
| 49 | GAG |
| 50 | CAT |
| 51 | CCA |
| 52 | CCC |
| 53 | CCG |
| 54 | CCT |
| 55 | CGA |
| 56 | CGC |
| 57 | CGG |
| 58 | CGT |
| 59 | CTA |
| 60 | CTC |
| 61 | CTG |
| 62 | CTT |
| 63 | GAA |
| 64 | GAG |
| 65 | GAG |
| 66 | GAT |
| 67 | GCA |
| 68 | GCC |
| 69 | GCG |
| 70 | GCT |
| 71 | GGA |
| 72 | GGC |
| 73 | GGG |
| 74 | GGT |
| 75 | GTA |
| 76 | GTC |
| 77 | GTG |
| 78 | GTT |
| 79 | TAA |
| 80 | TAC |
| 81 | TAG |
| 82 | TAT |
| 83 | TCA |
| 84 | TCC |
| 85 | TCG |
| 86 | TCT |
| 87 | TGA |
| 88 | TGC |
| 89 | TGG |
| 90 | TGT |
| 91 | TTA |
| 92 | TTC |
| 93 | TTG |
| 94 | TTT |

The term "cucumber-specific DNA sequence" indicates a polynucleotide sequence having a nucleotide sequence homology of more than 80%, preferably more than 85%, more preferably more than 90%, even more preferably more than 95%, still more preferably more than 97%, most preferably more than 99% with a sequence of the genome of the species Cucumis sativus that shows the greatest similarity to it, preferably in the case of markers for QTL-1, the part of the DNA sequence of cucumber accession PI 250147 flanking the QTL-1 markers.

The term "nucleotide sequence homology" as used herein denotes the presence of homology between two polynucleotides. Polynucleotides have "homologous" sequences if the sequence of nucleotides in the two sequences is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by visual inspection. Readily available sequence comparison and multiple sequence alignment algorithms are, respectively, the Basic Local Alignment Search Tool (BLAST) (Altschul et al., 1990; Altschul et al., 1997) and ClustalW programs, both available on the internet. Other suitable programs include, but are not limited to, GAP, Best-Fit, PlotSimilarity, and FASTA in the Wisconsin Genetics Software Package (Genetics Computer Group (GCG), Madison, Wis., USA) (Devereux et al., 1984).

The term "pm-h" as used herein refers to the putative powdery mildew resistance gene expressed in the hypocotyl, preferably as defined by the presence of the specific SNPs of Table 2.

TABLE 2

SNPs showing complete association with the powdery mildew resistance phenotype indicated herein as the QTL pm-h.

| SNP # | Indication | Resistant nucl. | Susceptible nucl. | Nucl. Position (SEQ ID NO) |
| --- | --- | --- | --- | --- |
| SNP1 | 39T>G | G | T | 39 (SEQ ID NO: 1) |
| SNP2 | 29G>A | A | G | 29 (SEQ ID NO: 2) |

The term "pm-1" as used herein refers to the putative powdery mildew resistance gene pm-leaf, preferably as defined by the presence of the specific mutations of Table 3.

TABLE 3

Mutations showing complete association with the powdery mildew resistance phenotype indicated herein as the QTL pm-1.

| Mutation | Indication nucl. | Resistant nucl. | Susceptible nucl. | Nucl. Position (SEQ ID NO) |
|---|---|---|---|---|
| SNP3 | 193C>T | T | C | 193 (SEQ ID NO: 3) |
|  |  | C | T |  |
| Insert1 | 221→AATTT | AATTT | — | 221-225 (SEQ ID NO: 4) |

The term "QTL-1" refers to the genomic region linked to closterovirus resistance as defined by the markers E16/M50-244, E16/M50-188, and/or E11/M48-251 as described in more detail in WO 02/22836, to which express reference is made in this context.

The term "offspring" plant refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

The term "hybrid" in the context of plant breeding refers to a plant that is the offspring of genetically dissimilar parents produced by crossing plants of different lines or breeds or species, including but not limited to the cross between two inbred lines.

As used herein, the term "inbred" means a substantially homozygous individual or line.

As used herein, the terms "introgression," "introgressed" and "introgressing" refer to both a natural and artificial process whereby genomic regions of one species, variety or cultivar are moved into the genome of another species, variety or cultivar, by crossing those species. The process may optionally be completed by backcrossing to the recurrent parent.

"Genetic engineering," "transformation" and "genetic modification" are all used herein as synonyms for the transfer of isolated and cloned genes into the DNA, usually the chromosomal DNA or genome, of another organism.

As used herein, the term "population" means a genetically heterogeneous collection of plants sharing a common genetic derivation.

As used herein, the term "variety" or "cultivar" means a group of similar plants that by structural or genetic features and/or performance can be distinguished from other varieties within the same species.

The terms "resistant" and "resistance" encompass both partial and full resistance to infection. A susceptible plant may either be non-resistant or have low levels of resistance to infection. The term is used to include such separately identifiable forms of resistance as "full resistance," "immunity," "intermediate resistance," "partial resistance," "hypersensitivity" and "tolerance."

"Full resistance" is referred to as complete failure of the disease to develop after infection, and may either be the result of failure of the disease to enter the cell (no initial infection) or may be the result of failure of the agent to multiply in the cell and infect subsequent cells (no subliminal infection, no spread).

The term "susceptible" is used herein to refer to a plant having no resistance to the disease resulting in the plant being affected by the disease, resulting in disease symptoms. The term "susceptible" is therefore equivalent to "non-resistant."

The term "hybrid" in the context of nucleic acids refers to a double-stranded nucleic acid molecule, or duplex, formed by hydrogen bonding between complementary nucleotide bases. The terms "hybridize" or "anneal" refer to the process by which single strands of nucleic acid sequences form double-helical segments through hydrogen bonding between complementary bases.

The term "probe" refers to a single-stranded oligonucleotide sequence that will form a hydrogen-bonded duplex with a complementary sequence in a target nucleic acid sequence analyte or its cDNA derivative.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T en G/C content) of primer. A pair of bi-directional primers consists of one forward and one reverse primer as commonly used in the art of DNA amplification such as in PCR amplification. It will be understood that "primer," as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical base pairing. The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di- or tri-ester method, the diethylphosphoramidate method and the solid support method disclosed in e.g. U.S. Pat. No. 4,458, 066. The primers may be labeled, if desired, by incorporating means detectable by for instance spectroscopic, fluorescence, photochemical, biochemical, immunochemical, or chemical means. Template-dependent extension of the oligonucleotide primer(s) is catalyzed by a polymerizing agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyze primer- and template-dependent DNA synthesis. Known DNA polymerases include, for example, $E.$ $coli$ DNA polymerase I or its Klenow fragment, T4 DNA polymerase, and Taq DNA polymerase. The reaction conditions for catalyzing DNA synthesis with these DNA polymerases are known in the art. The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve. The PCR method is well described in handbooks and known to the skilled person. After amplification by PCR, the target polynucleotides may be detected by hybridization with a probe polynucleotide which forms a stable hybrid with that of the target sequence under stringent to moderately stringent hybridization and wash conditions. If it is expected that the probes will be essentially completely complementary (i.e., about 99% or greater) to the target sequence, stringent conditions will be used. If some mismatching is expected, for example if variant strains are expected with the result that the probe will not be completely complementary, the stringency of hybridization may be lessened. However, conditions are chosen which rule out nonspecific/adventitious binding. Conditions which affect hybridization, and which select against nonspecific binding are known in the art, and are described in, for example, Sambrook and Russell, 2001. Generally, lower salt concentration and higher temperature increase the stringency of hybridization conditions.

The phrase "stringent hybridization conditions" refers to conditions under which a polynucleotide will hybridize to its target subsequence, typically in a complex mixture of nucleic acids, but to essentially no other sequences. Stringent conditions are sequence-dependent and will be different in different circumstances. Longer sequences hybridize specifically at higher temperatures. An extensive guide to the hybridization of nucleic acids is found in Tijssen, 1993. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. Additional guidelines for determining hybridization parameters are provided in numerous references (e.g. in Ausubel, et al. 1999).

DESCRIPTION OF THE PREFERRED EMBODIMENTS

Producing Double Resistant Plants

The purpose of breeding programs in agriculture and horticulture is to enhance the performances of plants by improving their genetic composition. In essence, this improvement accrues by increasing the frequency of the most favorable alleles for the genes influencing the performance characteristics of interest. Wild plant lines provide a rich resource of genetic and phenotypic variation. Traditionally, agricultural or horticultural practice makes use of this variation by selecting a wild plant line or its offspring for having desired genotypic or potential phenotypic properties, crossing it with a line having additional desired genotypic or potential phenotypic properties and selecting from amongst the offspring plant those plants that exhibit (an increased frequency of) the desired genotypic or potential phenotypic properties. A growing understanding and utilization of the laws of Mendelian inheritance in combination with molecular genetic tools have in the past century facilitated this selection process. For example, methods for selecting plants for having desired genotypic or potential phenotypic properties have become available based on testing said plant for the presence of a quantitative trait locus (QTL), i.e. for the presence of a chromosomal region containing alleles associated with the expression of a continuously distributed (quantitative) phenotypic trait. Usually a QTL is characterized by one or more markers that statistically associate to the quantitative variation in the phenotypic trait and is essentially synonymous to a gene. QTL mapping allows for the identification of candidate loci affecting the expression of a trait of interest. In plant breeding, it allows for marker-assisted selection (MAS), i.e. the selection of plants having favorable alleles by detecting in those plants the QTL associated markers.

One of the major problems in breeding programs of cultivated plants is the existence of negative genetic correlation between separate traits. This is for example the case with the negative genetic correlation between reproductive capacity and production in various disease-resistant plant lines. Understanding emerges to show that introgressions of DNA from the genome of one plant line into another may interfere with or affect the expression of basic reproductive traits.

Likewise, attempt to introgress resistance-conferring gene sequences from one plant into another may remove resistance traits already present in the recipient line.

Knowledge of the inheritance of various traits allows e.g. for the selection of lines homozygous for a QTL associated with disease resistance. Use of the knowledge of the genetic origin and location of a desired trait in a breeding program will increases the accuracy of the predicted breeding outcome and speeds up selection compared to conventional breeding programs. For instance, the fact that the genetic basis of a desired trait is heritably linked with another trait helps to increase uniformity for those two traits among the offspring, because a parent homozygous for the desired alleles will pass them to most offspring which will appear as a reduced segregation in the offspring.

As stated above, the present inventors discovered plants that were resistant to both closterovirus and powdery mildew. Such plants were hitherto not known. Attempts to introgress DNA from closterovirus resistant lines into an already powdery mildew resistant plant line, or vice versa had previously shown unsuccessful.

The present inventors furthermore discovered that in double resistant plants, the genes for resistance to closterovirus and powdery mildew are so closely linked that in effect they are co-inherited as if a single unit. Such a genetic configuration between genes so closely linked is sometimes also referred to as alleles (genes) being in coupling phase (in cis). In such cases, it is generally accepted that the genes reside on a single chromosome. In fact, when reference is made to the presence of the genes or the QTLs on a single chromosome, it is meant that they are in coupling phase.

The present inventors discovered that in double resistant plants, the genes for resistance to closterovirus and powdery mildew are present on linkage group 4. According to Horejsi et al. (2000), linkage group 4 of *Cucumis sativus* L also comprises genes for resistance to downy mildew (dm) resistance. LG 4 may be further characterized by (either) one or a combination of the following RFLP markers (as determined by the Software package INTMAP, Keygene, Wageningen, The Netherlands; map position in cM in brackets): CsC032a/E1 (25.9); CsP357/H3 (31.7); CsC588/H3 (34.2); CsC477H3 (35.3); CsC694/E5 (38.5); CsP347/H3 (38.5); CsC365/E1 (41); CsC386/E1 (41); CsC230/E1 (41.7); CsP064/E1 (45.5).

A definitive chromosome number has not yet been assigned to the cucumber chromosome on which QTL1 for closterovirus resistance and pm-l and pm-h for powdery mildew resistance are located. However, the chromosome may be designated by reference to the linkage group (LG 4) on which these and other genomic regions are located. The term linkage group is used herein to refer to a physical genomic unit on which the resistance-conferring alleles are located, and which has the same hierarchical level as a chromosome.

The implications of the finding that the genes for closterovirus en pm resistance are on a single chromosome are twofold.

First, it is very advantageous for breeding purposes to have genes located on a single chromosome, more preferably even on a small contiguous chromosome segment, as they will be passed on jointly to offspring plants. As a result of the physical linkage between the genes responsible for the powdery mildew-resistance and those responsible to the closterovirus-resistance, the offspring plants of a cross wherein the double resistant plant of the present invention is used as a parent plant provides for low frequencies of segregation in offspring plants.

Second, this knowledge may assist in plant breeding as it provides for a possible explanation of why the two traits are so difficult to combine into a single plant line. Without wishing to be bound by any theory, it is believed that the specific location of the QTL responsible for the closterovirus resistance and selection for that QTL hindered the formation of desirable introgressions or at least allowed for very few desirable introgressions to occur. The QTLs associated with powdery mildew resistance and the QTL for closterovirus resistance were situated in such close proximity, that introgression of a QTL for a second resistance trait (e.g. closterovirus) into a plant line already having a first resistance (e.g. powdery mildew) could result in (partial) loss of the first resistance trait. In the instances that a plant line has both QTLs for powdery mildew resistance (pm-l and pm-h), introgression of the QTL for closterovirus resistance can only occur into a very small section of the genome, without "damaging" the genetic information underlying the powdery mildew resistance.

Thus, apart from the finding that the various resistance genes were located in a single chromosome, it was found that when both powdery mildew resistance alleles were present in the double resistant plants, the QTL associated with closterovirus resistance (QTL-1) was situated in between the two QTLs associated with PM resistance (pm-h and pm-l). This finding may at least in part further explain the observed low frequency of recombination into the desired genotype. Also, it presupposes at least three possible scenarios of how such plants may come into existence, allowing for several reproducible methods for their production:

A first method would comprise introgressing the closterovirus-resistance-conferring locus (QTL-1 as defined herein) from a plant of a first line of interest into a powdery mildew resistant plant of a second line of interest possessing the two PM-resistance-conferring loci pm-h and pm-l. If this is to result in a genetic background of the second line of interest, the method would involve the introgression of QTL-1 into a genomic region in between the two PM-resistance-conferring loci pm-h and pm-l, in order to result in a genomic DNA sequence assembly having the configuration pm-l-QTL-1-pm-h in an offspring plant having the genetic background of the second line of interest (See FIG. 1). Based hereon it is predicted that only a double homologous recombination event (i.e. one event for each crossover) in a specific region of a single chromosome is capable of resulting in the double resistant phenotype of both closterovirus and PM resistance in the genetic background of the second line of interest. The establishment of the proper introgression in offspring plants may be monitored by using the QTL-1, pm-l and pm-h specific markers.

Figure 2:
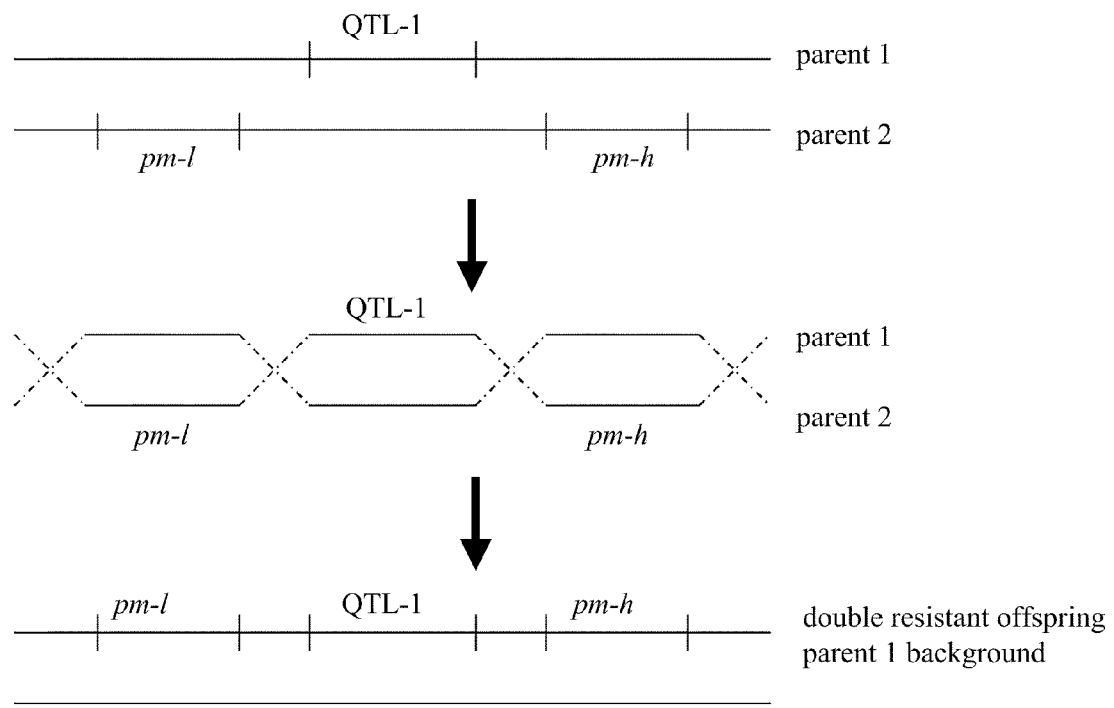

In a second method, one might wish to combine the resistance traits in a different genetic background, e.g. in the first line of interest. Such a method might comprise introgressing both PM-resistance-conferring loci pm-h and pm-l from a plant of a second line of interest into a closterovirus resistant plant of a first line of interest that possesses the QTL-1 locus. In this case, the method would involve the introgression of both the pm-h and pm-l loci independently on either side of the QTL-1 locus, in order to result in a genomic DNA sequence assembly having the configuration pm-l-QTL-1-pm-h in an offspring plant having the genetic background of the first line of interest (See FIG. 2). Based on this configuration, it is predicted that at least two double homologous recombination events (i.e. four crossover events) in specific regions of a single chromosome are required to result in the double resistant phenotype of both closterovirus and PM resistance. Again, the establishment of the proper introgression in offspring plants may be monitored by using the QTL-1, pm-l and pm-h specific markers.

The above may explain why introgression of CYSDV resistance from e.g. a wild accession into e.g. a PM resistant commercially valuable cucumber line is a very rare event. It may also explain why the introgression of both PM resistance loci from e.g. a wild accession into e.g. a closterovirus-resistant commercially valuable cucumber line is an even rarer event.

Recombination is the exchange of information between two homologous chromosomes during meiosis. In a recombinant plant, DNA that is originally present on a specific location within the chromosome is exchanged for DNA from another plant (i.e. maternal for paternal or vice versa). In a double recombinant this exchange occurred twice, e.g. on both sides of a gene/locus. In order to exchange only the required material, and maintain the valuable original information on the chromosome as much as possible, this will usually require four crossover events to occur (see above). The normal way to find such a double recombinant, is to screen a population of F2-plants. This population must be of sufficient size in order to detect the rare (low frequency) double recombinants. The frequency of double recombination is the product of the frequencies of the single recombinants. For instance, a recombinant in a 10 cM area can be found with a frequency of 10%, and double recombinants are found with a frequency of 10%×10%=1% (1 centimorgan is defined as 1% recombinant progeny in a testcross).

One way to circumvent this problem of low frequencies, is to perform "parallel recombination." Basically this means that the two recombination events are allowed to occur separately in two different plants, after which the recombination events are combined into one plant by simple crossing and selection in the resulting F2. This results in a reduction of the number of plants to be screened.

Figure 3:
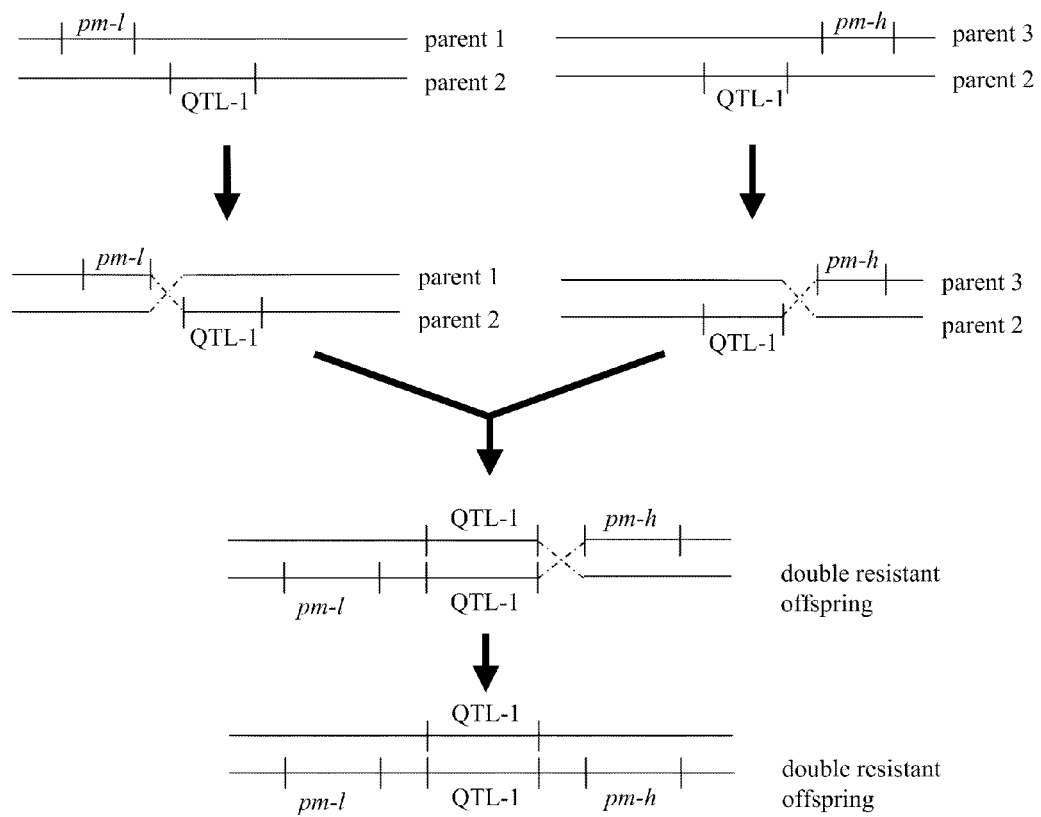
Figure 4:
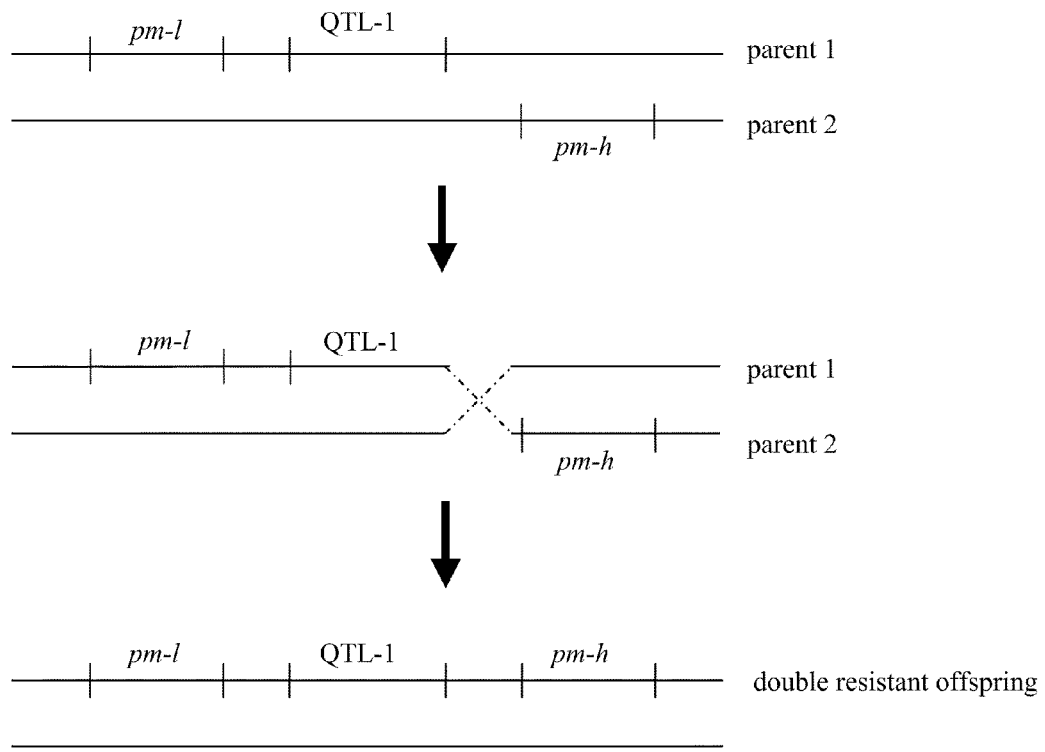
Figure 5:
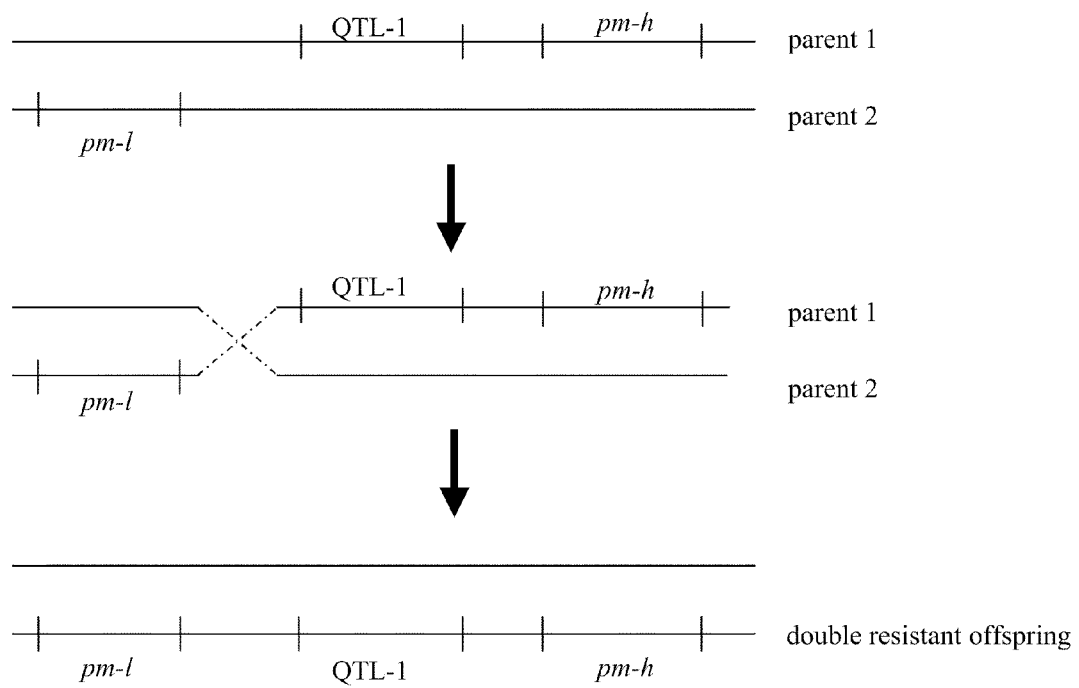
Figure 6:
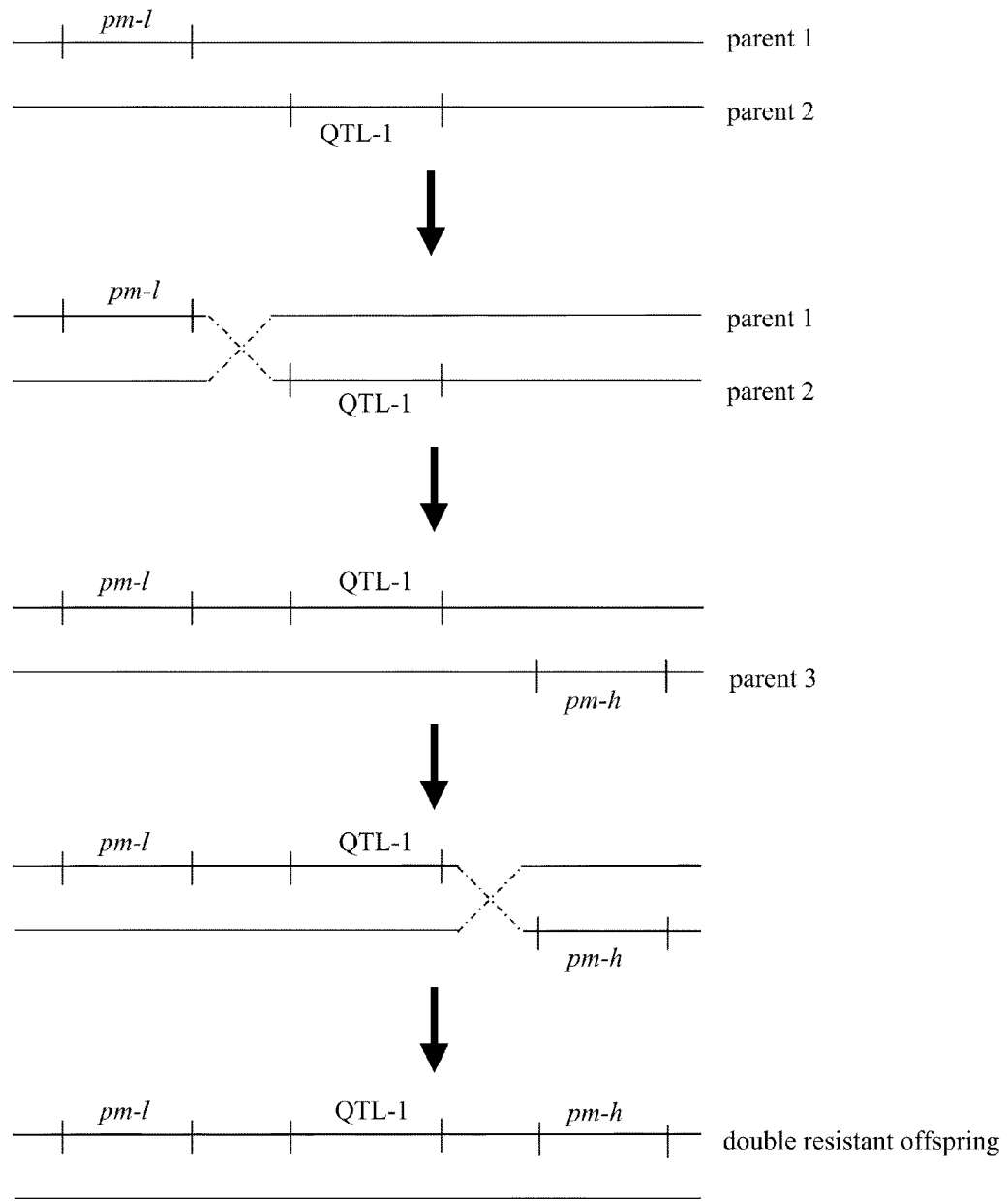
Figure 7:
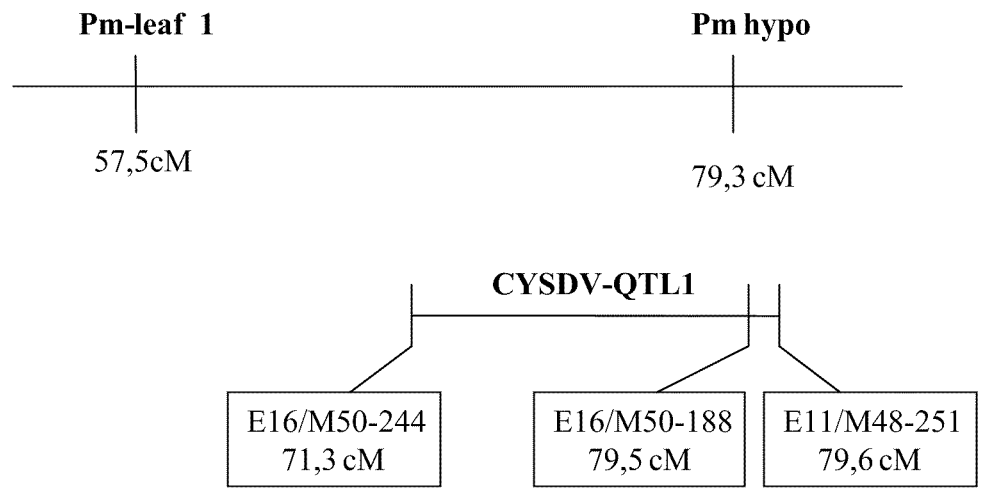
FIG. 7 shows the location of the various genes for powdery mildew resistance (pm) from *Cucumis sativus* NPI and for closterovirus resistance (QTL-1) from *C. sativus* Khira in a single linkage group. Pm-leaf 1 is equivalent to pm-l as used herein and Pm hypo is equivalent to pm-h as used herein.

Therefore, a third method for producing a double resistance plant would comprise introgressing one of the two PM-resistance-conferring loci pm-h or pm-l from first line of interest into a closterovirus resistant plant of a second line of interest that possesses the QTL-1 locus to result in a genomic DNA sequence assembly having the configuration pm-l-QTL-1 or QTL-1-pm-h, and introgressing the other of the two PM-resistance-conferring loci pm-h or pm-l from a third line of interest into another closterovirus resistant plant of a second line of interest that possesses the QTL-1 locus to result in a genomic DNA sequence assembly having the configuration QTL-1-pm-h or pm-l-QTL-1 (See FIG. 3). Subsequently offspring plants comprising introgressions from each individual recombination are crossed to result in a genomic DNA sequence assembly having the configuration pm-l-QTL-1-pm-h (See FIG. 3). Again, the establishment of the proper introgression in the various offspring plants may be monitored by using the QTL-1, pm-l and pm-h specific markers on the basis of which plants are selected for further crossings. Other methods may be derived by the skilled person from the FIGS. 4-6.

A method for limiting the number of plants to be screened may for instance be performed as follows: cross two individuals, one comprising both PM-resistance alleles (pm-l and pm-h) and one comprising the QTL resistance allele QTL-1. Select plants having 1 cross-over between one of the pm alleles and QTL-1 as follows: if the genetic distance between the two end points of the two pm alleles is 10 cM and the QTL1 is located in the middle (so 5 cM between QTL1 and either one of pm-l or pm-h), then such a recombination between QTL1 and either pm-locus occurs in a frequency of 5%. Therefore, first screen 200 offspring plants of the cross, of which 10 will be recombinants type A and 10 recombinants type B. Self the thus identified recombinants and screen 10 plants of the progeny for homozygotes by running markers flanking both QTL-1 and the pm-locus. Make 10 crosses between homozygotes A×B (10A's crossed with 10 B's) and in the resulting F2's screen 10 plants to find 1 double recombinant. In the end this will deliver 10 independent double recombinants. The number of plants screened in total then amounts to 500, whereas in the conventional method this would require the screening of 4000 plants to result in 10 independent double recombinants (distance of 5 cM between QTL-1 and either pm-locus, with frequency of double recombinants being 0.05×0.05=0.25%).

The present invention now provides for better models for marker assisted selection (MAS). The invention therefore relates to methods of plant breeding and to methods to select plants, in particular cucumber plants, particularly cultivated cucumber plants as breeder plants for use in breeding programs or cultivated cucumber plants for having desired genotypic or potential phenotypic properties, in particular related to producing valuable cucumber fruits, also referred to herein as commercially valuable plants. Herein, a cultivated plant is defined as a plant being purposely selected or having been derived from a plant having been purposely selected in agricultural or horticultural practice for having desired genotypic or potential phenotypic properties, in particular a plant obtained by inbreeding.

Double resistant plants of the present invention may for instance have the genotype AABBcc, AABbcc, AaBBcc or AaBbcc, wherein "A" is the resistant genotype based on the dominant pm-l locus, and "a" its corresponding non-resistant allele; "B" is the resistant genotype based on the dominant QTL-1 locus, and "b" its corresponding susceptible allele; and "c" is the resistant genotype based on the recessive pm-h locus. Thus, the double resistant plants of the invention both include homozygous plants as well as hybrid plants. These genotypes may be acquired by producing the following crosses (genotype of parent gametes): ABc×ABc; ABc×Abc; ABc×aBc; ABc×abc, and Abc×aBc. Thus it can be seen that a plant producing the gamete abc (which plant is not resistant, except for pm-h) can nonetheless be used to produce a double-resistant (hybrid) plant of the invention. In a particularly preferred embodiment, the double resistant plant of the invention is an inbred plant, homozygous for the resistance alleles.

Since the pm-h locus is a recessive locus, it cannot be monitored in the F1 or BC1 by using bioassays, that is if a susceptible parent is used to produce the F1/BC1 (as is common in breeding). Therefore, it is of particular advantage that the establishment of the proper introgression in offspring plants may be monitored by using the QTL-specific markers as provided herein. By using MAS or MAB methods, the skilled person is therefore provided with methods for selecting plants.

The present invention thus also provides methods for selecting a plant of the species *Cucumis sativus* exhibiting resistance towards cucumber closterovirus and cucumber powdery mildew comprising detecting in said plant the presence on a single chromosome of QTL-1 as defined herein, and at least one of the QTLs pm-l and pm-h as defined herein. In a preferred method of the invention for selecting such a plant the method comprises:

a) providing a sample of genomic DNA from a cucumber plant;

b) detecting in said sample of genomic DNA at least one molecular marker linked to a QTL selected from the group consisting of QTL-1, pm-l and pm-h, more preferably detecting at least two molecular markers from said group wherein one marker detects closterovirus resistance and the other marker detects powdery mildew resistance.

The step of providing a sample of genomic DNA from a cucumber plant may be performed by standard DNA isolation methods well known in the art.

The step of detecting a molecular marker (step b) may in a preferred embodiment, comprise the use of a set of bi-directional primers that were used in the AFLP method to produce the amplification product that later proved to be a suitable marker for the QTL. Such a set of primers is herein referred to as the primers that define the AFLP marker or marker-specific primers. Bi-directional means that the orientation of the primers is such that one functions as the forward and one as the reverse primer in an amplification reaction of nucleic acid.

Alternatively, the step of detecting a molecular marker (step b) may in another preferred embodiment, comprise the use of the a nucleic acid probe having a base sequence which is substantially complementary to the nucleic acid sequence defining said molecular marker and which nucleic acid probe specifically hybridizes under stringent conditions with a nucleic acid sequence defining said molecular marker. A suitable nucleic acid probe may for instance be a single strand of the amplification product corresponding to the marker.

The step of detecting a molecular marker (step b) may also comprise the performance of a nucleic acid amplification reaction on said genomic DNA to detect one or more QTLs. This can suitable be done by performing a PCR reaction using a set of marker-specific primers. In a preferred embodiment, said step b) comprises the use of at least one set of primers defining an AFLP marker for said QTL, or a set of primers which specifically hybridize under stringent conditions with a nucleic acid sequence of an AFLP marker for said QTL.

The step of detecting an amplified DNA fragment having the predicted length or the predicted nucleic acid sequence of step d) is preferably performed such that the amplified DNA fragment has a length that corresponds (plus or minus a few bases, e.g. a length of one, two or three bases more or less) to the expected length as based on a similar reaction with the same primers with the DNA from the plant in which the marker was first detected or the nucleic acid sequence that corresponds (has a homology of more than 80%, preferably more than 90%, more preferably more than 95%, even more preferably more than 97%, still more preferably more than 99%) to the expected sequence as based on the sequence of the marker associated with that QTL in the plant in which said marker was first detected. The skilled person is aware that markers that are absent in resistant plants, while they were present in the susceptible parent(s) (so-called trans-markers), may also be useful in assays for detecting resistance among offspring plants, although testing the absence of a marker to detect the presence of a specific trait is not optimal.

The step of detecting an amplified DNA fragment having the predicted length or the predicted nucleic acid sequence may be performed by standard gel-electrophoresis techniques or by using automated DNA sequencers. The methods need not be described here as they are well known to the skilled person.

In order to detect in a plant the presence of two QTLs on a single chromosome, chromosome painting methods may also be used. In such methods at least a first QTL and at least a second QTL may be detected in the same chromosome by in situ hybridization or in situ PCR techniques. Such techniques may also be used to assess the position of QTL-1 relative to pm-l and pm-h in said chromosome and are known in the art (e.g. vide Jiang et al., 1995). More conveniently, the fact that two QTLs are present on a single chromosome may be confirmed by determining that they are in coupling phase, i.e. that the traits show reduced segregation when compared to genes residing on separate chromosomes.

Molecular Markers and QTLs

Molecular markers are used for the visualization of differences in nucleic acid sequences. This visualization is possible due to DNA-DNA hybridization techniques after digestion with a restriction enzyme (RFLP) and/or due to techniques using the polymerase chain reaction (e.g. STS, microsatellites, AFLP). All differences between two parental genotypes will segregate in a mapping population (e.g., $BC_1$, $F_2$; see FIG. 2) based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a low genetic distance between markers on a chromosome. Comparing all recombination frequencies will result in the most logical order of the molecular markers on the chromosomes. This most logical order can be depicted in a linkage map (Paterson, 1996). A group of adjacent or contiguous markers on the linkage map that is associated with an increased level of resistance to a disease, e.g. to a reduced incidence of acquiring the disease upon infectious contact with the disease agent and/or a reduced lesion growth rate upon establishment of infection, pinpoints the position of a QTL associated with resistance to that disease.

The markers identified herein may be used is various aspects of the invention as will now be illustrated. Aspects of the invention are not be limited to the use of the markers identified herein. It is stressed that the aspects may also make use of markers not explicitly disclosed herein or even yet to be identified. Other than the genetic unit "gene," on which the phenotypic expression depends on a large number of factors that cannot be predicted, the genetic unit "QTL" denotes a region on the genome that is directly related to a phenotypic quantifiable trait. Thus, while genes per se bear little or no relation to plant breeding, a QTL is directly applicable to plant breeding. The present inventors have now discovered that the QTLs as defined herein for closterovirus-resistance and powdery mildew resistance in cucumber should have a specific constitution relative to each other in the genome of offspring plants. The inventors made this discovery on the basis of the observation that the presence of a string of contiguous genomic markers belonging to the different QTLs on a single chromosome in the genome of cucumber correlated to the presence both phenotypic resistance traits and they showed that this genomic organization could be inherited according to normal Mendelian laws of inheritance.

The QTLs as identified herein are located on a single chromosome or linkage group and their location is best characterized by a number of otherwise arbitrary markers. In the present investigations amplified fragment length polymorphism (AFLP) markers, single nucleotide polymorphisms (SNPs), and insertion mutation markers were used, although restriction fragment length polymorphism (RFLP) markers, microsatellite markers (e.g. SSRs), sequence-characterized amplified region (SCAR) markers, cleaved amplified polymorphic sequence (CAPS) markers or isozyme markers or combinations of these markers might also have been used. In general, a QTL may span a region of several million bases. Therefore, providing the complete sequence information for the QTL is practically unfeasible but also unnecessary, as the way in which the QTL is first detected—through the observed correlation between the presence of a string of contiguous genomic markers and the presence of a particular phenotypic trait—allows one to trace amongst a population of offspring plants those plants that have the genetic potential for exhibiting a particular phenotypic trait. By providing a non-limiting list of markers, the present invention thus provides for the effective utility of the QTLs in a breeding program.

A marker is specific for a particular line of breed. Thus, a specific trait is associated with a particular marker. The markers as indicated in the present application do not only indicate the location of the QTL, they also correlate to the presence of the specific phenotypic trait in a plant. It is important to note that the contiguous genomic markers that indicate the location of the QTL on the genome are in principal arbitrary or non-limiting. In general, the location of a QTL is indicated by a contiguous string of markers that exhibit statistical correlation to the phenotypic trait. Once a marker is found outside that string (i.e. one that has a LOD-score below a certain threshold, indicating that the marker is so remote that recombination in the region between that marker and the QTL occurs so frequently that the presence of the marker does not correlate in a statistically significant manner to the presence of the phenotype) the boundaries of the QTL are set. Thus, it is also possible to indicate the location of the QTL by other markers located within that specified region.

It is further important to note that the contiguous genomic markers can also be used to indicate the presence of the QTL (and thus of the phenotype) in an individual plant, i.e. they can be used in marker assisted selection (MAS) procedures. In principle, the number of potentially useful markers is limited but may be very large, and the skilled person may easily identify additional markers to those mentioned in the present application. Any marker that is linked to the QTL, e.g. falling within the physically boundaries of the genomic region spanned by the markers having established LOD scores above a certain threshold thereby indicating that no or very little recombination between the marker and the QTL occurs in crosses; as well as any marker in linkage disequilibrium to the QTL; as well as markers that represent the actual causal mutations within the QTL, may be used in MAS procedures. This means that the markers identified in the application as associated to the QTLs, such as the AFLP markers E16/M50-244, E16/M50-188, and E11/M48-251 for QTL-1, are mere examples of markers suitable for use in MAS procedures. Moreover, when the QTL, or the specific trait-conferring part thereof, is introgressed into another genetic background (i.e. into the genome of another plant species), then some markers may no longer be found in the offspring although the trait is present therein, indicating that such markers are outside the genomic region that represents the specific trait-conferring part of the QTL in the original parent line only and that the new genetic background has a different genomic organization. Such markers of which the absence indicates the successful introduction of the genetic element in the offspring are called "trans markers" and may be equally suitable in MAS procedures under the present invention.

Upon the identification of the QTL, the QTL effect (the resistance) may for instance be confirmed by assessing resistance in $BC_2S_1$ progenies segregating for the QTLs under investigation. The assessment of the resistance may suitably be performed by using a resistance bioassay as known in the art for both cucumber closterovirus and cucumber powdery mildew. For instance, the CYSDV isolate kept under accession no. PV-0592/EWSN_6 in the collection of the DSMZ-Deutsche Sammlung von Mikroorganismen und Zellkulturen GmbH (Braunschweig, Germany) may be used and experimental infection may be brought about through transmission by for instance *Bemisia tabaci* (B biotype). Also, (field) trials under natural infection conditions may be conducted to assess the resistance to CYSDV or other closteroviruses. Powdery mildew resistance may be assessed by artificial inoculation of plant materials. The markers provided by the present invention may very suitably be used for detecting the presence of one or more QTLs of the invention in a suspected powdery mildew and/or closterovirus-resistant cucumber plant, and may therefore be used in methods involving marker-assisted breeding and selection of powdery mildew and closterovirus resistant cucumber plants. Preferably, detecting the presence of a QTL of the invention is performed with at least one of the markers for a QTL as defined herein. The present invention therefore relates in another aspect to a method for detecting the presence of a QTL for powdery mildew and/or closterovirus-resistance, comprising detecting the presence of a nucleic acid sequence of said QTL in a suspected powdery mildew and/or closterovirus-resistant cucumber plant, which presence may be detected by the use of the said markers.

The nucleotide sequence of a QTL of the present invention may for instance be resolved by determining the nucleotide sequence of one or more markers associated with said QTL and designing internal primers for said marker sequences that may then be used to further determine the sequence the QTL outside of said marker sequences. For instance the nucleotide sequence of the AFLP markers from Tables 2, 3 and 4 may be obtained by isolating said markers from the electrophoresis gel used in the determination of the presence of said markers in the genome of a subject plant, and determining the nucleotide sequence of said markers by for instance dideoxy chain terminating methods, well known in the art.

In embodiments of such methods for detecting the presence of a QTL in a suspected powdery mildew and/or closterovirus-resistant cucumber plant, the method may also comprise the steps of providing a oligonucleotide or polynucleotide capable of hybridizing under stringent hybridization conditions to a nucleic acid sequence of a marker linked to said QTL, preferably selected from the markers of Tables 2, 3 and 4, contacting said oligonucleotide or polynucleotide with digested genomic nucleic acid of a suspected powdery mildew and/or closterovirus-resistant cucumber plant, and determining the presence of specific hybridization of said oligonucleotide or polynucleotide to said digested genomic nucleic acid.

Preferably said method is performed on a nucleic acid sample obtained from said suspected powdery mildew and/or closterovirus-resistant cucumber plant, although in situ hybridization methods may also be employed. Alternatively, and in a more preferred embodiment, the skilled person may, once the nucleotide sequence of the QTL has been determined, design specific hybridization probes or oligonucleotides capable of hybridizing under stringent hybridization conditions to the nucleic acid sequence of said QTL and may use such hybridization probes in methods for detecting the presence of a QTL of the invention in a suspected powdery mildew and/or closterovirus-resistant cucumber plant.

A marker for the locus of a major closterovirus resistance gene may be obtained by the selective amplification of fragments of cucumber DNA from resistant individuals and sensitive individuals descending from parental varieties:
wherein said fragments have been subjected to a digestion phase with restriction enzymes (e.g. EcoRI and MseI) followed by ligation in order to attach at the extremities of the fragments supplementary adapters for primers that have, at their extremity, one or more specific nucleotides, wherein one of the primers of the primer pair is labeled for the purpose of detection;

the separation of the amplification products, by gel electrophoresis under denaturing conditions, and the comparison of the gel electrophoresis profiles obtained with mixtures of fragments derived from resistant offspring and mixtures coming from sensitive offspring, with the fragments originating from parental varieties, in order to identify polymorphic bands that are genetically linked to the resistance locus. Said identification is followed by a validation step in which verification occurs on all individuals and the genetic recombination rate between the marker and the resistance locus is calculated.

In principle, individual AFLP markers as used herein have a designated marker code. This code defines two primers, optionally in combination with a figure indicating the length of the amplification product of the primers in a defined accession (see also description for Table 1 hereinabove). An AFLP marker thus defines a single or double-stranded DNA fragment as obtained by performing an amplification reaction on cucumber genomic DNA, which in the case of the indicated accession results in a fragment of the indicated length. Furthermore, the marker comprises in a 5'-3' direction a sequence consisting of a first primer sequence, a cucumber-specific DNA sequence and a second primer sequence, and its complement. The cucumber-specific DNA sequence thus being flanked by the two primers. The term "cucumber-specific DNA sequence" denotes the nucleotide sequence of the region flanked by the respective primers and represents the sequence amplified from cucumber accession Khira PI250147, as described in patent application WO 02/22836 by using the primers specified, or a sequence having a sequence homology thereto of at least 90%, preferably at least 95%, most preferably at least 98%.

Production of Powdery Mildew and Closterovirus-Resistant Cucumber Plants by Transgenic Methods According to another aspect of the present invention, a nucleic acid (preferably DNA) sequence comprising at least QTL-1 and one, preferably both of pm-l and pm-h or resistance-conferring parts thereof, may be used for the production of a double-resistant cucumber plant of the invention. In this aspect, the invention provides for the use of QTLs as defined herein or resistance-conferring parts thereof, for producing a double-resistant cucumber plant, which use involves the introduction of a nucleic acid sequence comprising said QTL in a suitable recipient plant. As stated, said nucleic acid sequence may be derived from a suitable closterovirus and/or powdery mildew-resistant donor plant. A suitable source for the closterovirus resistance locus identified herein as QTL-1 is cucumber landrace Khira, PI250147, originating from Pakistan. A number of PM resistant cucumber cultivars together with their commercial sources are for instance listed on World Wide Website cuke.hort.ncsu.edu/cucurbit/cuke/cukemain.html. PM resistant plants may for instance be obtained through T. C. Wehner, cucumber gene curator for the Cucurbit Genetics Cooperative (CGC), Department of Horticultural Science, North Carolina State University, Raleigh, N.C. 27695-7609 U.S.A. The source of both pm loci as described herein is NPI, which was obtained by crossing Natsufushinari (PI 279465) with PI 200815. Accessions may for instance be obtained from the Centre for Genetic Resources, the Netherlands (CGN), Wageningen, The Netherlands. Several plant databases are available to assist in selecting a suitable repository collections, such as the ECP/GR Cucurbits Database hosted by the Center for the Conservation and Breeding of Agrodiversity (COMAV) in Valencia, Spain, or the Germplasm Resources Information Network (GRIN) hosted by the USDA's National Germplasm Resources Laboratory, Beltsville, Md. Other cucumber plants that exhibit resistance to either closterovirus or powdery mildew may also be utilized as resistance donor plants as the present invention describes how this material may be identified.

Once identified in a suitable donor plant, the nucleic acid sequence that comprises a QTL for closterovirus or powdery mildew-resistance, or a resistance-conferring part thereof, may be transferred to a suitable recipient plant by any method available. For instance, the said nucleic acid sequence may be transferred by crossing a closterovirus or powdery mildew-resistance donor plant with a susceptible recipient plant (i.e. by introgression), by transformation, by protoplast fusion, by a doubled haploid technique or by embryo rescue or by any other nucleic acid transfer system, optionally followed by selection of offspring plants comprising the QTL and exhibiting resistance. For transgenic methods of transfer a nucleic acid sequence comprising a QTL for closterovirus or powdery mildew-resistance, or a resistance-conferring part thereof, may be isolated from said donor plant by using methods known in the art and the thus isolated nucleic acid sequence may be transferred to the recipient plant by transgenic methods, for instance by means of a vector, in a gamete, or in any other suitable transfer element, such as a ballistic particle coated with said nucleic acid sequence.

Plant transformation generally involves the construction of an expression vector that will function in plant cells. In the present invention, such a vector comprises a nucleic acid sequence that comprises a QTL for closterovirus or powdery mildew resistance, or a resistance-conferring part thereof, which vector may comprise a closterovirus or powdery mildew-resistance-conferring gene that is under control of or operatively linked to a regulatory element, such as a promoter. The expression vector may contain one or more such operably linked gene/regulatory element combinations, provided that at least one of the genes contained in the combinations encodes for closterovirus or powdery mildew-resistance. The vector(s) may be in the form of a plasmid, and can be used, alone or in combination with other plasmids, to provide transgenic plants that are resistant to closterovirus and powdery mildew, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (See e.g. Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (See e.g. Kado, 1991). Methods of introducing expression vectors into plant tissue include the direct infection or co-cultivation of plant cells with *Agrobacterium tumefaciens*, Horsch et al., 1985). Descriptions of *Agrobacterium* vectors systems and methods for *Agrobacterium*-mediated gene transfer provided by Gruber and Crosby, 1993 and Moloney et al., 1989. See also, U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. General methods of culturing plant tissues are provided for example by Miki et al., 1993 and by Phillips, et al., 1988. A proper reference handbook for molecular cloning techniques and suitable expression vectors is Sambrook and Russell, 2001.

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (See, Sanford et al., 1987, 1993; Sanford, 1988, 1990; Klein et al., 1988, 1992). Another method for introducing DNA to plants is via the sonication of target cells (see Zhang et al., 1991). Alternatively, liposome or spheroplast fusion has been used to introduce expression vectors into plants (see e.g. Deshayes et al., 1985 and Christou et al., 1987). Direct uptake of DNA into protoplasts using $CaCl_2$ precipitation, polyvinyl alcohol or poly-L-ornithine has also been reported (see e.g., Hain et al. 1985 and Draper et al., 1982). Electroporation of protoplasts and whole cells and tissues has also been described (D'Halluin et al., 1992 and Laursen et al., 1994).

Other well known techniques such as the use of BACs, wherein parts of the cucumber genome are introduced into bacterial artificial chromosomes (BACs), i.e. vectors used to clone DNA fragments (100- to 300-kb insert size; average, 150 kb) in *Escherichia coli* cells, based on naturally occurring F-factor plasmid found in the bacterium *E. coli*. (Zhao and Stodolsky, 2004) may for instance be employed in combination with the BIBAC system (Hamilton, 1997) to produce transgenic plants.

Following transformation of cucumber target tissues, expression of the above described selectable marker genes allows for preferential selection of transformed cells, tissues and/or plants, using regeneration and selection methods now well known in the art.

Production of Closterovirus and Powdery Mildew-Resistant Cucumber Plants by Non-Transgenic Methods In an alternative embodiment for producing a closterovirus and powdery mildew-resistant cucumber plant, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbreeded in nature, is tissue cultured into a hybrid plant exhibiting the desirable combination of traits. More specifically, a first protoplast can be obtained from a cucumber plant or other plant line that exhibits resistance to infection by closterovirus or powdery mildew. A second protoplast can be obtained from a second cucumber or other plant variety, preferably a cucumber line that comprises commercially valuable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising one or more QTLs as described herein from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (Pierik, 1999).

The present invention also relates to a method of producing a closterovirus or powdery mildew-resistant cucumber plant comprising the steps of performing a method for detecting the presence of a quantitative resistance locus (QTL) associated with resistance to closterovirus or powdery mildew in a donor cucumber plant according to invention as described above, and transferring a nucleic acid sequence comprising at least one QTL thus detected, or a closterovirus or powdery mildew-resistance-conferring part thereof, from said donor plant to a closterovirus or powdery mildew-susceptible recipient cucumber plant. The transfer of said nucleic acid sequence may be performed by any of the methods previously described herein.

A preferred embodiment of such a method comprises the transfer by introgression of said nucleic acid sequence from a closterovirus or powdery mildew-resistant donor cucumber plant into a closterovirus or powdery mildew-susceptible recipient cucumber plant by crossing said plants. This transfer may thus suitably be accomplished by using traditional breeding techniques. QTLs are preferably introgressed into commercial cucumber varieties by using marker-assisted selection (MAS) or marker-assisted breeding (MAB). MAS and MAB involves the use of one or more of the molecular markers for the identification and selection of those offspring plants that contain one or more of the genes that encode for the desired trait. In the present instance, such identification and selection is based on selection of QTLs of the present invention or markers associated therewith. MAS can also be used to develop near-isogenic lines (NIL) harboring the QTL of interest, allowing a more detailed study of each QTL effect and is also an effective method for development of backcross inbred line (BIL) populations (see e.g. Nesbitt et al., 2001; van Berloo et al., 2001). Cucumber plants developed according to this embodiment can advantageously derive a majority of their traits from the recipient plant, and derive closterovirus and powdery mildew-resistance from the donor plant.

As discussed briefly above, traditional breeding techniques can be used to introgress a nucleic acid sequence encoding for closterovirus or powdery mildew resistance into a closterovirus and powdery mildew-susceptible recipient cucumber plant. In one method, which is referred to as pedigree breeding, a donor cucumber plant that exhibits resistance to closterovirus or powdery mildew and comprising a nucleic acid sequence encoding for closterovirus or powdery mildew resistance is crossed with a closterovirus or powdery mildew-susceptible recipient cucumber plant that preferably exhibits commercially desirable characteristics, such as, but not limited to, disease resistance, insect resistance, valuable fruit characteristics, etc. The resulting plant population (representing the F1 hybrids) is then self-pollinated and set seeds ($F_2$ seeds). The $F_2$ plants grown from the $F_2$ seeds are then screened for resistance to closterovirus and powdery mildew. The population can be screened in a number of different ways.

First, the population can be screened using a traditional disease screen. Such disease screens are known in the art. Preferably a quantitative bioassay is used. Second, marker-assisted selection can be performed using one or more of the hereinbefore-described molecular markers to identify those progeny that comprise a nucleic acid sequence encoding for closterovirus or powdery mildew-resistance. Other methods, referred to hereinabove by methods for detecting the presence of a QTL may be used. Also, marker-assisted selection can be used to confirm the results obtained from the quantitative bioassays, and therefore, several methods may also be used in combination.

Inbred closterovirus and powdery mildew-resistant cucumber plant lines can be developed using the techniques of recurrent selection and backcrossing, selfing and/or dihaploids or any other technique used to make parental lines. In a method of recurrent selection and backcrossing, closterovirus and powdery mildew-resistance can be introgressed into a target recipient plant (the recurrent parent) by crossing the recurrent parent with a first donor plant, which differs from the recurrent parent and is referred to herein as the "non-recurrent parent." The recurrent parent is a plant that is non-resistant or has a low level of resistance to closterovirus and powdery mildew and possesses commercially desirable characteristics, such as, but not limited to (additional) disease resistance, insect resistance, valuable fruit characteristics, etc. The non-recurrent parent exhibits closterovirus and powdery mildew resistance and comprises a nucleic acid sequence that encodes for closterovirus and powdery mildew resistance. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened for the desired characteristics, which screening may occur in a number of different ways. For instance, the population can be screened using phenotypic pathology screens or quantitative bioassays as known in the art. Alternatively, in stead of using bioassays, marker-assisted selection (MAS) can be performed using one or more of the hereinbefore described molecular markers, hybridization probes or polynucleotides to identify those progeny that comprise a nucleic acid sequence encoding for closterovirus and powdery mildew-resistance. Also, MAS can be used to confirm the results obtained from the quantitative bioassays. Again, the recessive nature of pm-h means that this gene cannot be screened in an $F_1$ or $BC_1$ population by using phenotypic screens such as resistance bioassays. The markers defined herein are therefore ultimately suitable to select proper offspring plants by genotypic screening.

Following screening, the $F_1$ hybrid plants that exhibit a closterovirus and powdery mildew-resistant phenotype or, more preferably, genotype and thus comprise the requisite nucleic acid sequence encoding for closterovirus and powdery mildew resistance are then selected and backcrossed to the recurrent parent for a number of generations in order to allow for the cucumber plant to become increasingly inbred. This process can be performed for two to five or more generations. In principle the progeny resulting from the process of crossing the recurrent parent with the closterovirus and powdery mildew-resistance non-recurrent parent are heterozygous for one or more genes that encode for closterovirus and powdery mildew-resistance.

It should be brought into mind that, for instance when introgressing both pm-l and pm-h loci into a plant line, the pm-h locus is recessive and the resistant phenotype will only occur in offspring plants under conditions wherein homozygous pm-h plants can be formed.

In general, a method of introducing a desired trait into a hybrid cucumber variety comprises the steps of:

(a) crossing an inbred cucumber parent with another cucumber plant that comprises one or more desired traits, to produce F1 progeny plants, wherein the desired trait is selected from the group consisting of closterovirus resistance and powdery mildew resistance;

(b) selecting said F1 progeny plants that have the desired trait to produce selected F1 progeny plants, preferably using molecular markers as defined herein;

(c) backcrossing the selected progeny plants with said inbred cucumber parent plant to produce backcross progeny plants;

(d) selecting for backcross progeny plants that have the desired trait and morphological and physiological characteristics of said inbred cucumber parent plant, wherein said selection comprises the isolation of genomic DNA and testing said DNA for the presence of at least one molecular marker for QTL-1, pm-l and/or pm-h, preferably as described herein;

(e) repeating steps (c) and (d) two or more times in succession to produce selected third or higher backcross progeny plants;

(f) optionally selfing selected backcross progeny in order to identify homozygous plants (g) crossing at least one of said backcross progeny or selfed plants with another inbred cucumber parent plant (preferably one that is pmhypo resistant, i.e. is homozygous pm-h) to generate a hybrid cucumber variety with the desired trait and all of the morphological and physiological characteristics of hybrid cucumber variety when grown in the same environmental conditions.

As indicated, the last backcross generation may be selfed in order to provide for homozygous pure breeding (inbred) progeny for closterovirus and powdery mildew-resistance. Thus, the result of recurrent selection, backcrossing and selfing is the production of lines that are genetically homogenous for the genes associated with closterovirus and powdery mildew resistance as well as other genes associated with traits of commercial interest.

Closterovirus and Powdery Mildew-Resistant Cucumber Plants and Seeds

The goal of plant breeding is to combine in a single variety or hybrid various desirable traits. For commercial crops, these traits may include resistance to diseases and insects, tolerance to heat and drought, reducing the time to crop maturity, greater yield, and better agronomic quality. Uniformity of plant characteristics such as germination and stand establishment, growth rate, maturity, and plant height may also be of importance.

Commercial crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid cucumber variety in a cucumber plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. Preferably, an inbred line should comprise homozygous alleles at about 95% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid cucumber plants can then be generated from this hybrid seed supply.

A closterovirus and powdery mildew-resistant cucumber plant, or a part thereof, obtainable by a method of the invention is an aspect of the present invention.

Another aspect of the present invention relates to a closterovirus and powdery mildew-resistant cucumber plant, or part thereof, comprising the QTLs in any configuration as described in detail above wherein at least one of said QTLs is not in its natural genetic background. The closterovirus and powdery mildew-resistant cucumber plants of the present invention can be of any genetic type such as inbred, hybrid, haploid, dihaploid or transgenic. Further, the plants of the present invention may be heterozygous or homozygous for the resistance traits, preferably homozygous. Although the QTLs of the present invention, as well as resistance-conferring parts thereof may be transferred to any plant in order to provide for a closterovirus and powdery mildew-resistant plant, the methods and plants of the invention are preferably related to plants of the species *Cucumis sativus*.

The closterovirus and powdery mildew-resistant inbred cucumber lines described herein can be used in additional crossings to create closterovirus and powdery mildew-resistant hybrid plants. For example, a first closterovirus and powdery mildew-resistant inbred cucumber plant of the invention can be crossed with a second inbred cucumber plant possessing commercially desirable traits such as, but not limited to, disease resistance, insect resistance, desirable fruit characteristics, etc. This second inbred cucumber line may or may not be closterovirus or powdery mildew-resistant. Preferably this line is homozygous for pm-h in order for this recessive trait to be expressed in the hybrid offspring plants.

Another aspect of the present invention relates to a method of producing seeds that can be grown into closterovirus and powdery mildew-resistant cucumber plants. In one embodiment, the method comprises the steps of providing a closterovirus and powdery mildew-resistant cucumber plant of the invention, crossing said closterovirus and powdery mildew-resistant plant with another cucumber plant, and collecting seeds resulting from said cross, which when planted, produce closterovirus and powdery mildew-resistant cucumber plants.

In another embodiment, the method comprises the steps of providing a closterovirus and powdery mildew-resistant cucumber plant of the invention, crossing said closterovirus and powdery mildew-resistant plant with a cucumber plant, collecting seeds resulting from said cross, regenerating said seeds into plants, selecting closterovirus and powdery mildew-resistant plants by any of the methods described herein, self-pollinating the selected plants for a sufficient number of generations to obtain plants that are fixed for an allele that confers closterovirus and powdery mildew-resistance in the plants, backcrossing the plants thus produced with cucumber plants having desirable phenotypic traits for a sufficient number of generations to obtain cucumber plants that are closterovirus and powdery mildew-resistant and have desirable phenotypic traits, and collecting the seeds produced from the plants resulting from the last backcross, which when planted, produce cucumber plants which are closterovirus and powdery mildew-resistant.

Table 4 shows in a matrix format the presence or the absence in the double resistant plants of markers which were known to be present either the pm-resistant or closterovirus-resistant parental origin (indicated as presence in resistant parent). The matrix further indicates the origin and relative position of AFLP markers associated with the double (PM and closterovirus) resistant plant lines. The "markers" indicated by the terms pm-l and pm-h indicate the central positions of the two respective powdery mildew resistance loci referred to herein. No position was established for the QTL-1 locus, although by using the positions of the closterovirus-associated markers it could be determined that the locus was situated in between the two pm loci. It is to be understood from the table, that Pool numbers 1-6 have acquired a shorter introgression from the closterovirus-resistant parent than have pool nrs. 10-15. The interpretation of the matrix is as follows: Marker E23/M40-M003 (56.9 cM), for instance, was present in the pm-resistant parent and is also present in the double resistant offspring, whereas marker E11/M80-M003 (79.1 cM) was present in the closterovirus-resistant parent but is absent in the double resistant offspring. Thus, marker E23/M40-M003 is a PM associated marker, which presence designates the presence of the pm-l associated genetic region in the plant line tested, while marker E11/M80-M003, on the other hand, represents a genetic region in the vicinity of the QTL-1 locus associated with closterovirus resistance but which is not essential for the expression of pm-hypo (pm-h) resistance.

TABLE 4

AFLP marker scores in double resistant plants of the invention.

| Marker Name | cM | Pool Nr. (pooled DNA from 10 plants) | | | | | | | | | | | | | |
|---|---|---|---|---|---|---|---|---|---|---|---|---|---|---|---|
| | | 1 | 2 | 3 | 4 | 5 | 6 | 7 | 8 | 10 | 11 | 12 | 13 | 14 | 15 |
| E23/M40-M004 | 56.9 | ▒ | ▒ | ▒ | ▒ | ▒ | ▒ | ▒ | ▒ | ▒ | ▒ | ▒ | ▒ | ▒ | ▒ |
| E23/M40-M003 | 56.9 | ▒ | ▒ | ▒ | ▒ | ▒ | ▒ | ▒ | ▒ | ▒ | ▒ | ▒ | ▒ | ▒ | ▒ |
| pm-l | 57.5 | | | | | | | | | | | | | | |
| E24/M46-M002 | 58.4 | ▒ | ▒ | ▒ | ▒ | ▒ | ▒ | ▒ | ▒ | ▒ | ▒ | ▒ | ▒ | ▒ | ▒ |
| E24/M46-M003 | 58.4 | ▒ | ▒ | ▒ | ▒ | ▒ | ▒ | ▒ | ▒ | ▒ | ▒ | ▒ | ▒ | ▒ | ▒ |
| E12/M91-M003 | 59.4 | + | + | + | + | + | + | +/- | +/- | ▒ | ▒ | ▒ | ▒ | ▒ | ▒ |
| E26/M43-M003 | 59.4 | + | + | + | + | + | + | +/- | +/- | ▒ | ▒ | ▒ | - | - | ▒ |
| E12/M91-M002 | 59.4 | - | - | - | - | - | - | +/- | +/- | ▒ | + | + | + | + | + |
| E26/M43-M002 | 59.4 | - | - | - | - | - | - | +/- | +/- | ▒ | ▒ | ▒ | ▒ | ▒ | ▒ |
| E14/M59-F-134 | 61.7 | + | + | + | + | + | + | + | + | + | + | + | + | + | + |
| E14/M59-F-200 | 63.9 | + | + | + | + | + | + | + | + | + | + | + | + | + | + |
| E16/M50-F-244 | 71.3 | ▒ | ▒ | ▒ | ▒ | ▒ | ▒ | ▒ | ▒ | ▒ | ▒ | ▒ | ▒ | ▒ | ▒ |
| E23/M38-M003 | 71.6 | ▒ | ▒ | ▒ | ▒ | ▒ | ▒ | ▒ | ▒ | ▒ | ▒ | ▒ | ▒ | ▒ | ▒ |
| E16/M50-F-108 | 73.7 | + | + | + | + | + | + | + | + | + | + | + | + | + | + |
| E16/M50-F-109 | 73.7 | - | - | - | - | - | - | - | - | - | - | - | - | - | - |
| P12/M11-F-146 | 74.7 | - | - | - | - | - | - | - | - | - | - | - | - | - | - |
| P12/M11-F-147 | 74.7 | + | + | + | + | + | + | + | + | + | + | + | + | + | + |
| E14/M59-267.64CS | 76 | - | - | - | - | - | - | - | - | - | - | - | - | - | - |
| E23/M40-M005 | 76.8 | ▒ | ▒ | ▒ | ▒ | ▒ | ▒ | ▒ | ▒ | ▒ | ▒ | ▒ | ▒ | ▒ | ▒ |
| S2/M14M15-M001 | 76.8 | + | + | + | + | + | + | + | + | + | + | + | + | + | + |
| S2/M14M15-M002 | 76.8 | - | - | - | - | - | - | - | - | - | - | - | - | - | - |
| E18/M59-F-148 | 78 | - | - | - | - | - | - | ? | - | - | - | - | - | - | - |
| E18/M59-F-149 | 78 | + | + | + | + | + | + | ? | + | + | + | + | + | + | + |
| E11/M80-M001 | 78.1 | ▒ | ▒ | ▒ | ▒ | ▒ | ▒ | ▒ | ▒ | ▒ | ▒ | ▒ | D | ▒ | ▒ |
| E11/M80-M002 | 79.1 | ▒ | ▒ | ▒ | ▒ | ▒ | ▒ | ▒ | ▒ | ▒ | ▒ | ▒ | ▒ | ▒ | ▒ |
| E11/M80-M004 | 79.1 | ▒ | ▒ | ▒ | ▒ | ▒ | ▒ | ▒ | ▒ | ▒ | ▒ | ▒ | ▒ | ▒ | ▒ |
| E11/M80-M003 | 79.1 | ▒ | ▒ | ▒ | ▒ | ▒ | ▒ | ▒ | ▒ | ▒ | ▒ | ▒ | ▒ | ▒ | ▒ |
| pm-h | 79.3 | | | | | | | | | | | | | | |
| E16/M50-F-188 | 79.5 | +/- | +/- | ▒ | ▒ | ▒ | ▒ | ▒ | ▒ | ▒ | ▒ | ▒ | ▒ | ▒ | ▒ |
| E16/M50-F-194 | 79.5 | +/- | +/- | + | + | + | + | + | + | + | + | + | + | + | + |
| E11/M48-F-251 | 79.6 | ▒ | ▒ | ▒ | ▒ | ▒ | ▒ | ▒ | ▒ | ▒ | ▒ | ▒ | ▒ | ▒ | ▒ |
| E23/M38-M005 | 79.6 | ▒ | ▒ | ▒ | ▒ | ▒ | ▒ | ▒ | ▒ | ▒ | ▒ | ▒ | ▒ | ▒ | ▒ |
| E23/M38-M001 | 80 | ▒ | ▒ | ▒ | ▒ | ▒ | ▒ | ▒ | ▒ | ▒ | ▒ | ▒ | ▒ | ▒ | ▒ |
| E23/M38-M004 | 80 | ▒ | ▒ | ▒ | ▒ | ▒ | ▒ | ▒ | ▒ | ▒ | ▒ | ▒ | ▒ | ▒ | ▒ |
| E26/M43-M004 | 80 | - | - | - | - | - | - | - | - | - | - | - | - | - | - |
| E11/M48-F-148 | 91.2 | - | - | - | - | - | - | - | - | - | - | - | - | - | - |

+ = homozygous present (high intensity band)
- = absent (no band)
+/- = heterozygous present (low intensity band)
D = intermediate presence (medium intensity band)
▒ = marker score (both presence [+] and absence [-] are informative as in PM resistant parent
▒ = marker score as in closterovirus resistant parent
□ = presence of marker in parent line not established

REFERENCES

Ausubel F M, Brent R, Kingston R E, Moore D D, Seidman J G, Smith J A, Struhl K (eds.) (1998) *Current Protocols in Molecular Biology* Wiley, New York.

Bai Y L, Huang C C, van der Hulst R, Meijer Dekens F, Bonnema G, Lindhout P (2003) "QTLs for tomato powdery mildew resistance (*Oidium lycopersici*) in *Lycopersicon parviflorum* G1.1601 co-localize with two qualitative powdery mildew resistance genes," *Mol. Plant. Microbe Interactions* 16:169-176.

Christou P, Murphy J E, and Swain W F (1987) "Stable transformation of soybean by electroporation and root formation from transformed callus," *Proc. Natl. Acad. Sci. USA* 84:3962-3966.

Deshayes A, Herrera-Estrella L, Caboche M (1985) "Liposome-mediated transformation of tobacco mesophyllprotoplasts by an *Escherichia coli* plasmid," *EMBO J.*, 4:2731-2737.

D'Halluin K, Bonne E, Bossut M, De Beuckeleer M, Leemans J (1992) *Plant Cell*, 4: 1495-1505.

Draper J, Davey M R, Freeman J P, Cocking E C and Cox B J (1982) "Ti plasmid homologous sequences present in tissues from *Agrobacterium* plasmid-transformed *Petunia* protoplasts," *Plant and Cell Physiol.*, 23:451-458.

Fanourakis N E (1984) Inheritance and linkage studies of the fruit epidermis structure and investigation of linkage relations of several traits and of meiosis in cucumber. Ph.D. Diss., Univ. of Wisconsin, Madison.

Hujieda K, and Akiya R (1962) "Inheritance of powdery mildew resistance and spine color on fruit in cucumber," *J. Jpn. Soc. Hort. Sci.*, 31:30-32.

Ganal M W (1996) "Isolation and analysis of high-molecular-weight DNA from plants," *Nonmammalian Genomic Analysis: A Practical Guide*. Academic Press Inc., San Diego, pp. 61-73.

Gruber M Y, Crosby W L (1993) "Vectors for plant transformation," *Methods in Plant Molecular Biology and Biotechnology*. CRC Press, Baton Rouge, L A, B R Glick, J E Thompson, eds, pp. 89-119.

Hain R, Stabel P, Czernilofsky A P, Steinbliss H H, Herrera-Estrella L, Schell J (1985) "Uptake, integration, expression and genetic transmission of a selectable chimaeric gene to plant protoplasts," *Mol. Gen. Genet.,* 199:161-168.

Hamilton C M. (1997) "A binary-BAC system for plant transformation with high-molecular-weight DNA," *Gene* 200: 107-116.

Horejsi T, Staub J E and Thomas C. (2000) "Linkage of random amplified polymorphic DNA markers to downy mildew resistance in cucumber (*Cucumis sativus* L.)," *Euphytica* 115 (2):105-113.

Horsch R B, Fraley R T, Rogers S G, Sanders P R, Lloyd A (1985) "A simple and general method for transferring genes into plants," *Science* 227:1229-1231.

Jiang J, Gill B S, Wang G L, Ronald P C and Ward D C (1995) "Metaphase and interphase fluorescence in situ hybridization mapping of the rice genome with bacterial artificial chromosomes," *Proc. Natl. Acad. Sci. USA,* 92:4487-4491.

Kado C I (1991) "Molecular mechanisms of crown gall tumorigenesis," *Crit. Rev. Plant Sci.* 10:1-32.

Klein T M, Gradziel T, Fromm M E, Sanford J C (1988) "Factors influencing gene delivery into *zea mays* cells by high velocity microprojectiles," *Biotechnology* 6:559-563.

Klein T M, Arentzen R, Lewis P A, and Fitzpatrick-McElligott S (1992) "Transformation of microbes, plants and animals by particle bombardment," *Bio/Technology* 10:286-291.

Kleine M, Cai D, Hermann R G, and Jung C (1995) "Physical mapping and cloning of a translocation in sugar beet (*Beta vulgaris* L.) carrying a gene for nematode (*Heterodera schachtii*) resistance from *B. procumbens*," *Theor. Application. Genet.* 90:399-406.

Kooistra E (1968) Powdery mildew resistance in cucumber. *Euphytica* 17:236-244.

Kooistra E (1971) "Inheritance of flesh and skin colors in powdery mildew resistant cucumbers (*Cucumis sativus* L.)," *Euphytica* 20:521-523.

Lui B H (1997) *Statistical Genomics: Linkage Mapping and QTL Analysis,* CRC Press. pp. 18-19.

Miki B L, Fobert P F, Charest P J, Iyer V N. (1993) "Procedures for Introducing Foreign DNA into Plants," *Methods in Plant Molecular Biology & Biotechnology,* CRC Press, Glick B R and Thompson J E (Eds.) pp. 67-88.

Moloney M M, Walker J M, Sharma K K (1989) "High efficiency transformation of *Brassica napus* using *Agrobacterium* vectors," *Plant Cell Rep* 8: 238-242.

Morishita M, Sugiyama K, Saito T, and Sakata Y (2003) "Review: Powdery Mildew Resistance in Cucumber," *JARQ* 37(1):7-14.

Nesbitt T C, Tanksley S D (2001) "fw2.2 directly affects the size of developing tomato fruit, with secondary effects on fruit number and photosynthate distribution," *Plant Physiol.,* 127:575-583.

Paterson A H (1996) "Mapping genes responsible for differences in phenotype," *Genome mapping in plants,* A. H. Paterson (ed.), R. G. Landes Company, pp. 41-54.

Phillips R L, Somers D A, Hibberd K A. (1988) "Cell/tissue culture and in vitro manipulation," *Corn and corn improvement,* 3rd ed., G. F. Sprague & J. W. Dudley, eds. Madison, Wis., USA, American Society of Agronomy, pp. 345-387.

Pierik, R. L. M. (1999) *In vitro Culture of Higher Plants,* 4th edition. Martinus Nijhoff Publishers, Dordrecht.

Sambrook J, and Russell D W (2001) *Molecular Cloning: A Laboratory Manual.* New York, N.Y., USA., Cold Spring Harbor Laboratory Press.

Sanford J C, Klein T M, Wolf E D, Allen N (1987) "Delivery of substances into cells and tissues using a particle bombardment process," *J. Particulate Sci. Technol.* 5:27-37.

Sanford J C (1988) "The biolistic process," *Trends in Biotechnology* 6:299-302.

Sanford J C (1990) "Biolistic plant transformation," *Physiologica Plantarum,* 79:206-209.

Sanford J C, Smith F D, and Russell J A (1993) "Optimizing the biolistic process for different biological applications," *Methods in Enzymology* 217:483-509.

Shanmugasundarum S, Williams P H, and Peterson C E (1971) "Inheritance of resistance to powdery mildew in cucumber. *Phytopathology* 61:1218-1221.

Shanmugasundarum S, Williams P H, and Peterson C E (1972) A recessive cotyledon marker gene in cucumber with pleiotropic effects," *HortScience* 7:555-556.

Tijssen P (1993) "Hybridization with Nucleic Acid Probes. Part I. Theory and Nucleic Acid Preparation," *Laboratory Techniques in Biochemistry and Molecular Biology,* Elsevier.

Van Berloo R, Aalbers H, Werkman A, Niks R E (2001) "Resistance QTL confirmed through development of QTL-NILs for barley leaf rust resistance," *Mol. Breeding,* 8:187-195.

Vos P, Hogers R, Bleeker M, Reijans M, van de Lee T, Hornes M, Frijters A, Pot J, Peleman J, Kuiper M (1995) "AFLP: a new technique for DNA fingerprinting," *Nucl. Acids Res.,* 23:4407-4414.

Zhang L, Cheng L, Xu N, Zhao M, Li C, Yuan J, and Jia S (1991) "Efficient transformation of tobacco by ultrasonication," *Biotechnology.* 9:996-997.

Zhao S, and Stodolsky M (2004) "Bacterial Artificial Chromosomes," *Methods in Molecular Biology,* Vol. 255, Humana Press Inc., Totowa, N.J., USA.

What is claimed is:

1. An inbred plant having resistance to *Cucurbit* yellow stunting disorder virus (CYSDV) and to cucumber powdery mildew, wherein said plant is of the species *Cucumis sativus*, said plant comprising, on a single chromosome, at least one quantitative trait locus (QTL) that confers CYSDV resistance and at least one QTL that confers powdery mildew resistance, wherein said at least one QTL that confers CYSDV resistance is linked to at least one marker selected from the group consisting of markers E16/M50-244, E16/M50-188, and E11/M48-251, and wherein said at least one QTL that confers powdery mildew resistance is linked to at least one marker selected from the group consisting of:

the single nucleotide polymorphism marker 39T→G in SEQ ID NO:1, the single nucleotide polymorphism marker 29G→A in SEQ ID NO:2, and markers E16/M50-F-194, E11/M48-F-251, and E23/M38-M001, or is linked to at least one marker selected from the group consisting of:

the single nucleotide polymorphism marker 193C→T in SEQ ID NO:3, the insertion mutation 5'-AATTT-3' at position 221 in SEQ ID NO:4, and markers E23/M40-M003, E24/M46-M002, E24/M46-M003, E12/M91-M003, E26/M43-M003, E14/M59-F-134 and E14/M59-F-200.

2. The inbred plant according to claim 1, wherein said plant comprises at least two QTLs that confer powdery mildew resistance, wherein a first of said at least two QTLs is linked to at least one marker selected from the group consisting of:

the single nucleotide polymorphism marker 39T→G in SEQ ID NO:1, the single nucleotide polymorphism marker 29G→A in SEQ ID NO:2, and markers E16/M50-F-194, E11/M48-F-251, and E23/M38-M001, and wherein a second of said at least two QTLs is linked to at least one marker selected from the group consisting of:

the single nucleotide polymorphism marker 193C→T in SEQ ID NO:3, the insertion mutation 5'-AATTT-3' at position 221 in SEQ ID NO:4, and
markers E23/M40-M003, E24/M46-M002, E24/M46-M003, E12/M91-M003, E26/M43-M003, E14/M59-F-134 and E14/M59-F-200.

3. The inbred plant according to claim 2, wherein said at least one QTL that confers CYSDV resistance is positioned in between said at least two QTLs that confer powdery mildew resistance.

4. A part of an inbred cucumber plant as defined in claim 1.

5. The inbred plant part according to claim 4, wherein said inbred plant part is a member selected from the group consisting of pollen, ovules, leaves, embryos, roots, root tips, anthers, flowers, fruits, stems, shoots, scions, rootstocks, seeds, protoplasts and calli.

6. F1 seed obtained by crossing a cucumber plant, as defined in claim 1, with a second cucumber plant, wherein said seed comprises:
   at least one marker for CYSDV resistance selected from the group consisting of markers E16/M50-244, E16/M50-188, and E11/M48-251, and
   at least one marker for powdery mildew resistance selected from the group consisting of:
      the single nucleotide polymorphism marker 39T→G in SEQ ID NO:1,
      the single nucleotide polymorphism marker 29G→A in SEQ ID NO:2,
      markers E16/M50-F-194, E11/M48-F-251, and E23/M38-M001,
   or is selected from the group consisting of:
      the single nucleotide polymorphism marker 192C→T in SEQ ID NO:3,
      the insertion mutation 5'AATTT-3' at position 221 in SEQ ID NO:4, and
      markers E23/M40-M003, E24/M46-M002, E24/M46-M003, E12/M91-M003, E26/M43-M003, E14/M59-F-134 and E14-M59-F-200.

7. The seed according to claim 6, wherein said second cucumber plant is susceptible to CYSDV and wherein said at least one marker for powdery mildew resistance is homozygously present.

8. The seed according to claim 6, wherein said second cucumber plant is an inbred plant.

9. A hybrid plant obtained by growing the seed of claim 4.

10. A part of the hybrid plant as defined in claim 9.

11. The plant part according to claim 10, wherein said plant part is a member selected from the group consisting of pollen, ovules, leaves, embryos, roots, root tips, anthers, flowers, fruits, stems, shoots, scions, rootstocks, seeds, protoplasts and calli.

12. A method for selecting a plant having resistance to CYSDV and to cucumber powdery mildew, wherein said plant is of the species *Cucumis sativus*, said method comprising performing a marker detection assay, wherein said assay comprises the steps of:
   a) obtaining a sample of nucleic acid from said plant;
   b) detecting in the sample from said plant the presence of at least one marker linked to CYSDV resistance selected from the group consisting of markers E16/M50-244, E16/M50-188, and E11/M48-251,
   c) detecting in the sample from said plant the presence of at least one marker linked to powdery mildew resistance selected from the group consisting of:
      the single nucleotide polymorphism marker 39T→G in SEQ ID NO:1,
      the single nucleotide polymorphism marker 29G→A in SEQ ID NO:2, and
      markers E16/M50-F-194, E11/M48-F-251, and E23/M38-M001,
   or is selected from the group consisting of:
      the single nucleotide polymorphism marker 193C→T in SEQ ID NO:3,
      the insertion mutation 5'-AATTT-3' at position 221 in SEQ ID NO:4,
      markers E23/M40-M003, E24/M46-M002, E24/M46-M003, E12/M91-M003, E26/M43-M003, E14/M59-F-134 and E14/M59-F-200.

13. The method according to claim 12, wherein step c) comprises:
   detecting the presence in the sample from said plant of at least one marker linked to a first cucumber powdery mildew resistance-conferring QTL indicated by SNP marker 39→G in SEQ ID NO:1, SNP marker 29→A in SEQ ID NO:2, and markers E16/M50-F-194, E11/M48-F-251, and E23/M38-M001; and
   detecting in the sample from said plant the presence of at least one marker linked to a second cucumber powdery mildew resistance conferring QTL indicated by SNP marker 193C→T in SEQ ID NO:3, insertion mutation 5'-AATTT-3' at position 221 in SEQ ID NO:4, and markers E23/M40-M003, E24/M46-M002, E241M46-M003, E12/M91-M003, E26/M43-M003, E14/M59-F-134 and E14/M59-F-200.

14. The method according to claim 12, wherein steps b) or c) or both comprise the use of at least one set of primers defining said marker(s), or at least one nucleic acid probe having a base sequence which is substantially complementary to the nucleic acid sequence defining said marker(s) and which nucleic acid probe specifically hybridizes under stringent conditions with nucleic acid sequence defining said marker(s).

15. The method according to claim 12, comprising establishing that said markers are present on the same chromosome and in coupling phase by demonstrating a reduced segregation between the markers in crossing experiments when compared to uncoupled markers.

16. An inbred plant selected by the method according to claim 12.

17. A method of producing a plant of the species *Cucumis sativus* which plant exhibits resistance to CYSDV and to cucumber powdery mildew, comprising the steps of:
   a) selecting a first cucumber plant that comprises a QTL that confers resistance CYSDV, by detecting in the genome of said plant the presence of at least one marker linked to the CYSDV resistance-conferring QTL indicated by markers E16/M50-244, E16/M50-188, and E11/M48-251;
   b) selecting a second cucumber plant that comprises at least one QTL that confers resistance to cucumber powdery mildew
   by detecting in the genome of said plant the presence of at least one marker linked to a first cucumber powdery mildew resistance-conferring QTL indicated by the following markers:
      the single nucleotide polymorphism marker 39T→G in SEQ ID NO:1,
      the single nucleotide polymorphism marker 29G→A in SEQ ID NO:2, and markers E16/M50-F-194, E11/M48-F-251, and E23/M38-M001;

or by detecting in the genome of said plant the presence of at least one marker linked to a second cucumber powdery mildew resistance-conferring QTL indicated by the following markers:
the single nucleotide polymorphism marker 193C→T in SEQ ID NO:3,
the insertion mutation 5'-AATTT-3' at position 221 in SEQ ID NO:4, and
markers E23/M40-M003, E24/M46-M002, E24/M46-M003, E12/M91-M003, E26/M43-M003, E14/M59-F-134 and E14/M59-F-200;

c) crossing said plants from step a) and step b) to produce F1 seeds;

d) growing an amount of F1 seeds into F1 plants, generating a further offspring population from said F1 plants by crossing or selfing, and e) selecting from among said further offspring plants a plant that comprises at least one marker linked to the CYSDV resistance-conferring QTL as defined in step a) and at least one marker linked to the cucumber powdery mildew resistance-conferring QTL as defined in step b).

18. The method according to claim 17, wherein the step of selecting a second cucumber plant in step b) comprises selecting a second cucumber plant having one of said first or second cucumber powdery mildew resistance-conferring QTLs, and wherein said method further comprises the step of:

f) selecting a third cucumber plant having another of said first or second cucumber powdery mildew resistance-conferring QTLs;

g) crossing the F1 plants obtained in step e) with said third cucumber plant to produce further offspring plants, and h) selecting from among the offspring plants a plant that comprises the CYSDV resistance-conferring QTL as defined in step a) and both the cucumber powdery mildew resistance-conferring QTLs as defined in step b).

19. The method according to claim 18, wherein the step of selecting a cucumber plant that comprises a QTL that confers resistance to cucumber powdery mildew as defined in steps b), e), f), or h) comprises:
detecting the presence in the genome of said plant of at least one marker liked to a first cucumber powdery mildew resistance-conferring QTL indicated by SNP marker 39T→G in SEQ ID NO:1, SNP marker 29G→A in SEQ ID NO:2, and markers E16/M50-F-194, E11/M48-F-251, and E23/M38-M001; and
detecting in the genome of said plant the presence of at least one marker linked to a second cucumber powdery mildew resistance-conferring QTL indicated by SNP marker 193C→T in Sec ID NO:3, insertion mutation 5'-AATTT-3' at position 221 in SEQ ID NO:4, and markers E23/M40-M003, E24/M46-M002, E24/M46-M003, E12/M91-M003, E26/M43-M003, E14/M59-F-134 and E14/M59-F-200.

20. The method according to claim 18, wherein at least one of the steps a), b), e), f) or h) comprise the step of providing a sample of genomic DNA from said plant and detecting in said sample of genomic DNA said at least one marker.

21. A method of producing a plant of the species *Cucumis sativus* which plant exhibits resistance to CYSDV and to cucumber powdery mildew, comprising the steps of:
a) selecting a plant of the species *Cucumis sativus* that comprises QTLs that confer resistance towards CYSDV and cucumber powdery mildew by performing the method of claim 12;
b) inbreeding said plant to produce a plant line homozygous for said QTLs
c) crossing said plants from step a) and step b) to produce F1 seeds, and
d) growing said F1 seeds into F1 offspring plants.

22. An inbred plant, or a part thereof, obtainable by the method according to claim 17.

* * * * *

UNITED STATES PATENT AND TRADEMARK OFFICE
CERTIFICATE OF CORRECTION

| | | |
|---|---|---|
| PATENT NO. | : 8,895,812 B2 | Page 1 of 1 |
| APPLICATION NO. | : 12/112519 | |
| DATED | : November 25, 2014 | |
| INVENTOR(S) | : Hofstede et al. | |

It is certified that error appears in the above-identified patent and that said Letters Patent is hereby corrected as shown below:

Title Page, Item (30), please delete "05077528" and insert --05077528.7--

In the Claim

Column 42, Line 7, Claim 19 please delete "liked" and insert --linked--

Column 42, Line 14, Claim 19 please delete "Sec" and insert --SEQ--

Signed and Sealed this
Seventeenth Day of March, 2015

Michelle K. Lee
*Director of the United States Patent and Trademark Office*

SEQUENCE LISTING

<160> NUMBER OF SEQ ID NOS: 4

<210> SEQ ID NO 1
<211> LENGTH: 156
<212> TYPE: DNA
<213> ORGANISM: Cucumis sativus

<400> SEQUENCE: 1

```
gtcgtcttcg cctatgcaga caaaataaat gcttgtttga gtctagccaa aaatggtgta      60
gaacagttga tcacagttcc tacggactat aacattagaa acacctttga caaattttct     120
gtgttttgca tagaccatag tggtaattga caggcg                              156
```

```
<210> SEQ ID NO 2
<211> LENGTH: 290
<212> TYPE: DNA
<213> ORGANISM: Cucumis sativus

<400> SEQUENCE: 2
tcataatgac acgtaatgat tgtcagagaa aatttataga aacctttttgt tcaactatcc      60 aacaaattac aatcaaggca cttctggaat gagatagtca gctgctaagc agatctcaaa     120
gggagaagag aaaaatattc acatcacaga ctataacaaa ggtttgaatc ttaaggccaa     180
caaacaactt tgtagatgtc aaaaaaaaat gtacgaaata aacgataaaa gatgcatgtc     240
tctctttcta gatgaattat caaagatctc tgactacaag aggggatata                 290

<210> SEQ ID NO 3
<211> LENGTH: 263
<212> TYPE: DNA
<213> ORGANISM: Cucumis sativus

<400> SEQUENCE: 3
tttttatctt ctcccaagta ccgcaaccga gaggattcat cttcatgttc ttccaagtgc      60
cacagccaga ggatttatct tcaccttccc ccatgtgttg carccgagag gattcatctt     120
cagcttctct caggtgccgc aatcgagagg attcatgttc atcttctccc aggtgctaca     180
atcgaaagaa tttatcttca tcttctctta ggkgccacaa tcgagagggt ttatcttcat     240
ctttcctcat gtgtggcaac cga                                             263

<210> SEQ ID NO 4
<211> LENGTH: 281
<212> TYPE: DNA
<213> ORGANISM: Cucumis sativus

<400> SEQUENCE: 4
tcgataattc aggctcgcaa ctcaaattgc attgagaatc ttttagggag aagtatgtat      60
tatagcagag gatgaggatc agagaatatt gagatcgtcg tagttaggat caaagtgaac     120
ccacggattg attgactgga tccggtagga tgaaggcctt tgacttagtg gataagagag     180
gtccttgtaa aatattattt ttcatttaga ccttgatttt aatttggact atgaatcata     240
tttgacaatt gtaggatcaa accgaaggtg caaagaatat t                         281
```